United States Patent [19]
Anthony et al.

[11] Patent Number: 5,571,835
[45] Date of Patent: Nov. 5, 1996

[54] INHIBITORS OF FARNESYL-PROTEIN TRANSFERASE

[75] Inventors: Neville J. Anthony, Hatfield; S. Jane deSolms, Norristown; Samuel L. Graham, Schwenksville, all of Pa.

[73] Assignee: Merck & Co., Inc., Rahway, N.J.

[21] Appl. No.: 315,059

[22] Filed: Sep. 29, 1994

[51] Int. Cl.$^6$ .......................... A61K 31/40; C07D 207/09
[52] U.S. Cl. ...................... 514/428; 548/568; 548/314.7; 548/465; 548/466; 548/468; 546/201; 546/210; 540/602; 540/603; 540/607; 540/609; 514/212; 514/315; 514/323; 514/326; 514/397; 514/414
[58] Field of Search .............................. 548/568; 514/428

[56] References Cited

U.S. PATENT DOCUMENTS

| | | | |
|---|---|---|---|
| 5,043,268 | 8/1991 | Stock | 435/15 |
| 5,141,851 | 8/1992 | Brown et al. | 435/15 |
| 5,238,922 | 8/1993 | Graham et al. | 514/18 |
| 5,326,773 | 7/1994 | De Solms et al. | 514/336 |
| 5,340,828 | 8/1994 | Graham et al. | 514/357 |
| 5,352,705 | 10/1994 | Deana et al. | 514/630 |

FOREIGN PATENT DOCUMENTS

| | | |
|---|---|---|
| 0456180A1 | 11/1991 | European Pat. Off. . |
| 0618221A2 | 10/1994 | European Pat. Off. . |
| 2130590 | 6/1984 | United Kingdom . |
| WO91/16340 | 10/1991 | WIPO . |

OTHER PUBLICATIONS

Gibbs, J. B. et al., "Selective Inhibition of Farnesyl–Protein Transferase Blocks Ras Processing in Vivo", The Journal of Biological Chemistry, vol. 268, No. 11, pp. 7617–7620 (1993).

Goldstein, J. L. et al., "Nonfarnesylated Tetrapeptide Inhibitors of Protein Farnesyltransferase", The Journal of Biological Chemistry, vol. 266, No. 24 pp. 15575–15578 (1991).

James, G. L. et al., "Benzodiazepine Peptidomimetic BZA–5B Interrupts the MAP Kinase Activation Pathway in H–Ras–transformed Rat–1 Cells, but Not in Untransformed Cells", The Journal of Biological Chemistry, vol. 369, No. 44, pp. 27705–27714 (1994).

James, G. L. et al., "Benzodiazepine Peptidomimetics: Potent Inhibitors Of Ras Farnesylation in Animal Cells", Science, vol. 260, pp. 1937–1942 (1993).

Kohl, N. E. et al., "Selective Inhibition of ras–Dependent Transformation by a Farnesyltransferase Inhibitor", Science, vol. 260, pp. 1934–1937 (1993).

Kohl, N. E. et al., "Protein farnesyltransferase inhibitors block the growth of ras–dependent tumors in nude mice", Proc. Natl. Acad. Sci. USA, Med. Sciences, vol. 91, pp. 9141–9145 (1994).

Pompliano, D. L., "Steady–State Kinetic Mechanism of Ras Farnesyl:Protein Transferase", Biochemistry, vol. 31, pp. 3800–3807 (1992).

Primary Examiner—Johann Richter
Assistant Examiner—Laura L. Stockton
Attorney, Agent, or Firm—David A. Muthard; Mark R. Daniel

[57] ABSTRACT

The present invention comprises analogs of the $CA_1A_2X$ motif of the protein Ras that is modified by farnesylation in vivo. These $CA_1A_2X$ analogs inhibit the farnesylation of Ras. Furthermore, these $CA_1A_2X$ analogues differ from those previously described as inhibitors of Ras farnesyl transferase in that they have a prolyl like moiety in the $A_1$ position. Further contained in this invention are chemotherapeutic compositions containing these farnesyl transferase inhibitors and methods for their production.

19 Claims, No Drawings

INHIBITORS OF FARNESYL-PROTEIN TRANSFERASE

BACKGROUND OF THE INVENTION

The Ras gene is found activated in many human cancers, including colorectal carcinoma, exocrine pancreatic carcinoma, and myeloid leukemias. Biological and biochemical studies of Ras action indicate that Ras functions like a G-regulatory protein, since Ras must be localized in the plasma membrane and must bind with GTP in order to transform cells (Gibbs, J. et al., Microbiol. Rev. 53:17 1–286 (1989). Forms of Ras in cancer cells have mutations that distinguish the protein from Ras in normal cells.

At least 3 post-translational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Aaa is an aliphatic amino acid, the Xaa is any amino acid) (Willumsen et al., *Nature* 310:583–586 (1984)). Other proteins having this motif include the Ras-related GTP-binding proteins such as Rho, fungal mating factors, the nuclear lamins, and the gamma subunit of transducin.

Farnesylation of Ras by the isoprenoid farnesyl pyrophosphate (FPP) occurs in vivo on Cys to form a thioether linkage (Hancock et al., Cell 57:1167 (1989); Casey et al., Proc. Natl. Acad. Sci. USA 86:8323 (1989)). In addition, Ha-Ras and N-Ras are palmitoylated via formation of a thioester on a Cys residue near a C-terminal Cys farnesyl acceptor (Gutierrez et al., EMBO J. 8:1093–1098 (1989); Hancock et al., Cell 57:1167–1177 (1989)). Ki-Ras lacks the palmitate acceptor Cys. The last 3 amino acids at the Ras C-terminal end are removed proteolytically, and methyl esterification occurs at the new C-terminus (Hancock et al., ibid). Fungal mating factor and mammalian nuclear lamins undergo identical modification steps (Anderegg et al., *J. Biol. Chem.* 263:18236 (1988); Farnsworth et al., *J. Biol. Chem.* 264:20422 (1989)).

Inhibition of Ras farnesylation in vivo has been demonstrated with lovastatin (Merck & Co., Rahway, N.J.) and compactin (Hancock et al., ibid; Casey et at., ibid; Schafer et al., *Science* 245:379 (1989)). These drugs inhibit HMG-CoA reductase, the rate limiting enzyme for the production of polyisoprenoids and the farnesyl pyrophosphate precursor. It has been shown that a farnesyl-protein transferase using farnesyl pyrophosphate as a precursor is responsible for Ras farnesylation. (Reiss et al., Cell, 62:81–88 (1990); Schaber et at., *J. Biol. Chem.*, 265:14701–14704 (1990); Schafer et at., *Science*, 249:1133–1139 (1990); Manne et al., *Proc. Natl. Acad. Sci USA*, 87:7541–7545 (1990)).

Inhibition of farnesyl-protein transferase and, thereby, of farnesylation of the Ras protein, blocks the ability of Ras to transform normal cells to cancer cells. The compounds of the invention inhibit Ras farnesylation and, thereby, generate soluble Ras which, as indicated infra, can act as a dominant negative inhibitor of Ras function. While soluble Ras in cancer cells can become a dominant negative inhibitor, soluble Ras in normal cells would not be an inhibitor.

A cytosol-localized (no Cys-Aaa$^1$-Aaa$^2$-Xaa box membrane domain present) and activated (impaired GTPase activity, staying bound to GTP) form of Ras acts as a dominant negative Ras inhibitor of membrane-bound Ras function (Gibbs et al., *Proc. Natl. Acad. Sci. USA* 86:6630–6634(1989)). Cytosollocalized forms of Ras with normal GTPase activity do not act as inhibitors. Gibbs et al., ibid, showed this effect in Xenopus oocytes and in mammalian cells.

Administration of compounds of the invention to block Ras farnesylation not only decreases the amount of Ras in the membrane but also generates a cytosolic pool of Ras. In tumor cells having activated Ras, the cytosolic pool acts as another antagonist of membrane-bound Ras function. In normal cells having normal Ras, the cytosolic pool of Ras does not act as an antagonist. In the absence of complete inhibition of farnesylation, other farnesylated proteins are able to continue with their functions.

Farnesyl-protein transferase activity may be reduced or completely inhibited by adjusting the compound dose. Reduction of farnesyl-protein transferase enzyme activity by adjusting the compound dose would be useful for avoiding possible undesirable side effects resulting from interference with other metabolic processes which utilize the enzyme.

These compounds and their analogs are inhibitors of farnesyl-protein transferase. Farnesyl-protein transferase utilizes farnesyl pyrophosphate to covalently modify the Cys thiol group of the Ras CAAX box with a farnesyl group. Inhibition of farnesyl pyrophosphate biosynthesis by inhibiting HMG-CoA reductase blocks Ras membrane localization in vivo and inhibits Ras function. Inhibition of farnesyl-protein transferase is more specific and is attended by fewer side effects than is the case for a general inhibitor of isoprene biosynthesis.

Previously, it has been demonstrated that tetrapeptides containing cysteine as an amino terminal residue with the CAAX sequence inhibit Ras farnesylation (Schaber et al., ibid; Reiss et. at., ibid; Reiss et al., *PNAS*, 88:732–736 ( 1991 )). Previously described CA$_1$A$_2$X-type FPTase inhibitors contain acyclic amino acids in the second position. Incorporation of proline in the A 1 position in such inhibitors has been shown to be the least well tolerated amino acid substitution in that position (Reiss et al., *PNAS* (1991)). Such inhibitors may inhibit while serving as alternate substrates for the Ras farnesyl-transferase enzyme, or may be purely competitive inhibitors (U.S. Pat. 5,141,851, University of Texas).

Recently, it has been demonstrated that certain inhibitors of farnesyl-protein transferase selectively block the processing of Ras oncoprotein intracellularly (N.E. Kohl et at., *Science*, 260:1934–1937 (1993) and G.L. James et al., *Science*, 260:1937–1942 (1993).

Inhibitors of Ras farnesyl-protein transferase (FPTase.) have been described in two general classes. The first are analogs of farnesyl diphosphate (FPP), while the second class of inhibitors is related to the protein substrate for the enzyme, Ras. Almost all of the peptide derived inhibitors that have been described are cysteine containing molecules that are related to the CAAX motif that is the signal for protein prenylation. The exception to this generalization is a class of natural products known as the pepticinnamins (Omura, et at., J. Antibiotics 46:222 (1993).

It is, therefore, an object of this invention to develop tetrapeptide-based compounds which incorporate a cyclic amino acid in the second position, and which will inhibit farnesyl transferase and the post-translational functionalization of the oncogene Ras protein. It is a further object of this invention to develop chemotherapeutic compositions containing the compounds of this invention and methods for producing the compounds of this invention.

SUMMARY OF THE INVENTION

The present invention comprises analogs of the CAAX motif of the protein Ras that is modified by farnesylation in vivo. These CAAX analogs inhibit the farnesylation of Ras. Furthermore, these CAAX analogues differ from those previously described as preferred inhibitors of Ras farnesyl transferase in that they incorporate a cyclic amine moiety in the second amino acid position of the motif. Further contained in this invention are chemotherapeutic compositions containing these farnesyl transferase inhibitors and methods for their production.

The compounds of this invention are illustrated by the formulae:

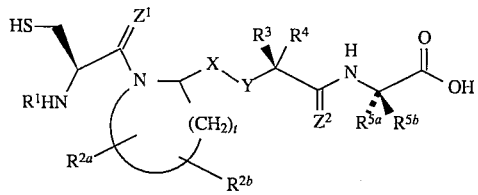

I

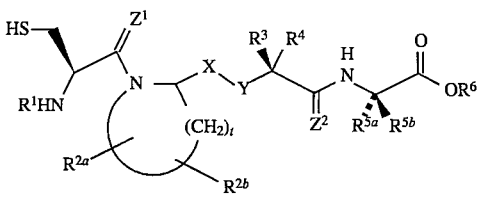

II

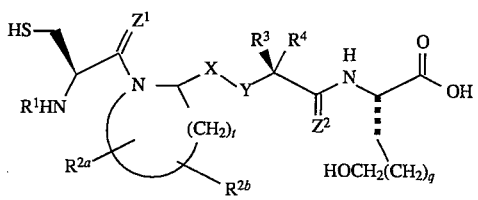

III

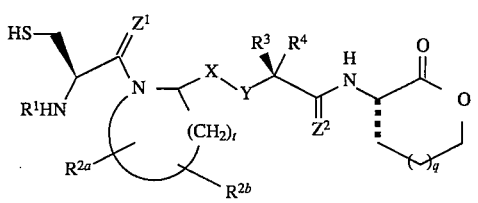

IV

DETAILED DESCRIPTION OF THE INVENTION

The compounds of this invention inhibit the farnesylation of Ras. In a first embodiment of this invention, the Ras farnesyl transferase inhibitors are illustrated by the formula I:

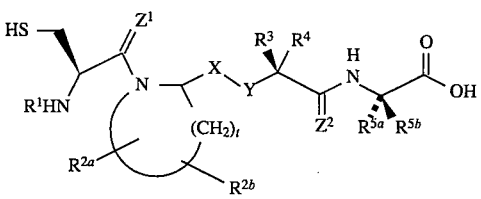

I wherein:
$R^1$ is selected from:
 a) hydrogen,
 b) $R^8S(O)_2$-, $R^8C(O)$-, $(R^8)_2NC(O)$- or $R^9OC(O)$-, and
 c) $C_1$–$C_6$ alkyl unsubstituted or substituted by aryl, heterocyclic, cycloalkyl, alkenyl, alkynyl, $R^8O$-, $R^8S(O)_m$-, $R^8C(O)NR^8$-, CN, $(R^8)_2N$-$C(NR^8)$-, $R^8C(O)$-, $R^8OC(O)$-, $N_3$, -$N(R^8)_2$, or $R^9OC(O)NR^8$-;

$R^{2a}$ and $R^{2b}$ are independently selected from:
 a) hydrogen,
 b) C1–C6 alkyl unsubstituted or substituted by alkenyl, $R^8O$-, $R^8S(O)_m$-, $R^8C(O)NR^8$-, CN, $(R^8)_2N$-$C(NR^8)$-, $R^8C(O)$-, $R^8OC(O)$-, $N_3$, -$N(R^8)_2$, or $R^9OC(O)NR^8$-,
 c) aryl, heterocycle, cycloalkyl, alkenyl, $R^8O$-, $R^8S(O)_m$-, $R^8C(O)NR^8$-, CN, $NO_2$, $(R_8)_2N$-$C(NR^8)$-, $R^8C(O)$-, $R^8OC(O)$-, $N_3$, -$N(R^8)_2$, or $R^9OC(O)NR^8$-, and
 d) $C_1$–$C_6$ alkyl substituted with an unsubstituted or substituted group selected from aryl, heterocyclic and $C_3$–$C_{10}$ cycloalkyl;

$R^3$ and $R^4$ are independently selected from:
 a) a side chain of a naturally occurring amino acid,
 b) an oxidized form of a side chain of a naturally occurring amino acid which is:
  i) methionine sulfoxide, or
  ii) methionine sulfone,
 c) substituted or unsubstituted $C_1$–$C_{20}$ alkyl, $C_2$–$C_{20}$ alkenyl, $C_3$–$C_{10}$ cycloalkyl, aryl or heterocyclic group, wherein the substituent is selected from F, Cl, Br, $N(R^8)_2$, $NO_2$, $R^8O$-, $R^8S(O)_m$-, $R^8C(O)NR^8$-, CN, $(R^8)_2N$-$C(NR^8)$-, $R^8C(O)$-, $R^8OC(O)$-, $N_3$, -$N(R^8)_2$, $R^9OC(O)NR^8$- and $C_1$–$C_{20}$ alkyl, and
 d) $C_1$–$C_6$ alkyl substituted with an unsubstituted or substituted group selected from aryl, heterocyclic and $C_3$–$C_{10}$ cycloalkyl; or
$R^3$ and $R^4$ are combined to form -$(CH_2)_s$-;

$R^{5a}$ and $R^{5b}$ are independently selected from:
 a) a side chain of a naturally occurring amino acid,
 b) an oxidized form of a side chain of a naturally occurring amino acid which is:
  i) methionine sulfoxide, or
  ii) methionine sulfone,
 c) substituted or unsubstituted $C_1$–$C_{20}$ alkyl, $C_2$–$C_{20}$ alkenyl, $C_3$–$C_{10}$ cycloalkyl, aryl or heterocycle group, wherein the substituent is selected from F, Cl,Br, $N(R^8)_2$, $NO_2$, $R^8O$-, $R^8S(O)_m$-, $_RC(O)NR^8$-, CN, $(R^8)_2N$-$C(NR^8)$-, $R^8C(O)$-, $R^8OC(O)$-, $N_3$, -$N(R^8)_2$, $R^9OC(O)NR^8$- and $C_1$–$C_{20}$ alkyl, and
 d) $C_1$–$C_6$ alkyl substituted with an unsubstituted or substituted group selected from aryl, heterocyclic and $C_3$–$C_{10}$ cycloalkyl;

$R^{5a}$ and $R^{5b}$ are combined to form —$(CH_2)_s$— wherein one of the carbon atoms is optionally replaced by a moiety selected from: $O, S(O)_m$, —NC(O)—, and —N($COR^8$)—;

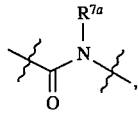  a)

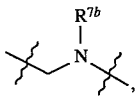  b)

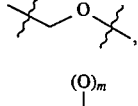  c)

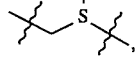  d)

e)

or $-CH_2-CH_2-$; f)

$R^{7a}$ is selected from
a) hydrogen,
b) unsubstituted or substituted aryl,
c) unsubstituted or substituted heterocycle,
d) unsubstituted or substituted cycloalkyl, and
e) $C_1-C_6$ alkyl substituted with hydrogen or an unsubstituted or substituted group selected from aryl, heterocycle and cycloalkyl;

$R^{7b}$ is selected from
a) hydrogen,
b) unsubstituted or substituted aryl,
c) unsubstituted or substituted heterocycle,
d) unsubstituted or substituted cycloalkyl,
e) $C_1-C_6$ alkyl substituted with hydrogen or an unsubstituted or substituted group selected from aryl, heterocycle and cycloalkyl,
f) a carbonyl group which is bonded to an unsubstituted or substituted group selected from aryl, heterocycle, cycloalkyl and $C_1-C_6$ alkyl substituted with hydrogen or an unsubstituted or substituted group selected from aryl, heterocycle and cycloalkyl, and
g) a sulfonyl group which is bonded to an unsubstituted or substituted group selected from aryl, heterocycle, cycloalkyl and $C_1-C_6$ alkyl substituted with hydrogen or an unsubstituted or substituted group selected from aryl, heterocycle and cycloalkyl;

$R^8$ is independently selected from hydrogen, $C_1-C_6$ alkyl and aryl;

$R^9$ is independently selected from $C_1-C_6$ alkyl and aryl; p0 $Z^1$ and $Z^2$ are independently $H_2$ or O, provided that $Z^1$ is not O when X-Y is $-C(O)N(R^{7a})-$;

m is 0, 1 or 2;
s is 4 or 5; and
t is 3, 4 or 5;
or the pharmaceutically acceptable salts thereof.

In a second embodiment of this invention the prodrugs of compounds of formula I are illustrated by the formula II:

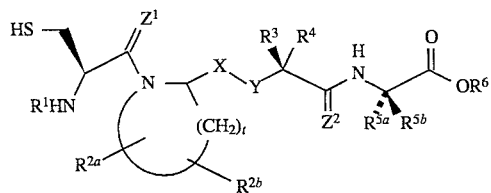

wherein:
$R^1$ is selected from:
a) hydrogen,
b) $R^8S(O)_2-$, $R^8C(O)-$, $(R^8)_2NC(O)-$ or $R^9OC(O)-$, and
c) $C_1-C_6$ alkyl unsubstituted or substituted by aryl, heterocyclic, cycloalkyl, alkenyl, alkynyl, $R^8O-$, $R^8S(O)_m-$, $R^8C(O)NR^8-$, CN, $(R^8)_2N-C(NR^8)-$, $R^8C(O)-$, $R^8OC(O)-$, $N_3$, $-N(R^8)_2$, or $R^9OC(O)NR^8-$;

$R^{2a}$ and $R^{2b}$ are independently selected from:
a) hydrogen,
b) $C_1-C_6$ alkyl unsubstituted or substituted by alkenyl, $R^8O-$, $R^8S(O)_m-$, $R^8C(O)NR^8-$, CN, $(R^8)_2N-C(NR^8)-$, $R^8C(O)-$, $R^8OC(O)-$, $N_3$, $-N(R^8)_2$, or $R^9OC(O)NR^8-$,
c) aryl, heterocycle, cycloalkyl, alkenyl, $R^8O-$, $R^8S(O)_m-$, $R^8C(O)NR^8-$, CN, $NO_2$, $(R^8)_2N$ $C(NR^8)-$, $R^8C(O)-$, $R^8OC(O)-$, $N_3$, $-N(R^8)_2$, or $R^9OC(O)NR^8-$, and
d) $C_1-C_6$ alkyl substituted with an unsubstituted or substituted group selected from aryl, heterocyclic and. $C_3-C_{10}$ cycloalkyl;

$R^3$ and $R^4$ are independently selected from:
a) a side chain of a naturally occurring amino acid,
b) an oxidized form of a side chain of a naturally occurring amino acid which is:
i) methionine sulfoxide, or
ii) methionine sulfone, and
c) substituted or unsubstituted $C_1-C_{20}$ alkyl, $C_2-C_{20}$ alkenyl, $C_3-C_{10}$ cycloalkyl, aryl or heterocyclic group, wherein the substituent is selected from F, Cl, Br, $N(R^8)_2$, $NO_2$, $R^8O-$, $R^8S(O)_m-$, $R^8C(O)NR^8-$, CN, $(R^8)_2N-C(NR^8)-$, $R^8C(O)-$, $R^8OC(O)-$, $N_3$, $-N(R^8)_2$, $R^9OC(O)NR^8-$ and $C_1-C_{20}$ alkyl, and
d) $C_1-C_6$ alkyl substituted with an unsubstituted or substituted group selected from aryl, heterocyclic and $C_3-C_{10}$ cycloalkyl; or
$R^3$ and $R^4$ are combined to form $-(CH_2)_s-$;

$R^{5a}$ and $R^{5b}$ are independently selected from:
a) a side chain of a naturally occurring amino acid,
b) an oxidized form of a side chain of a naturally occurring amino acid which is:
i) methionine sulfoxide, or
ii) methionine sulfone,
c) substituted or unsubstituted $C_1-C_{20}$ alkyl, $C_2-C_{20}$ alkenyl, $C_3-C_{10}$ cycloalkyl, aryl or heterocycle group, wherein the substituent is selected from F, Cl, Br, $N(R^8)_2$, $NO_2$, $R^8O-$, $R^8S(O)_m-$, $R^8C(O)NR^8-$, CN, $(R^8)_2N-C(NR^8)-$, $R^8C(O)-$, $R^8OC(O)-$, $N_3$, $-N(R^8)_2$, $R^9OC(O)NR^{8-}$ and $C_1-C_{20}$ alkyl, and
d) $C_1-C_6$ alkyl substituted with an unsubstituted or substituted group selected from aryl, heterocyclic and $C_3-C_{10}$ cycloalkyl; or
$R^{5a}$ and $R^{5b}$ are combined to form $-(CH_2)_s-$ wherein one of the carbon atoms is optionally replaced by a moiety selected from: O, $S(O)_m$, $-NC(O)-$, and $-N(COR^8)-$;

$R^6$ is
a) substituted or unsubstituted $C_1-C_8$ alkyl, wherein the substituent on the alkyl is selected from:
1) aryl,
2) heterocycle,
3) $-N(R^9)2$,
4) $-OR^8$, or
b)

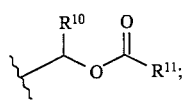;

X-Y is

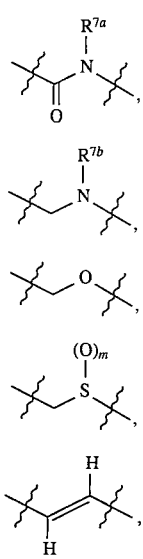

a)
b)
c)
d)
e)

or

—CH₂—CH₂—; f)

$R^{7a}$ is selected from
 a) hydrogen,
 b) unsubstituted or substituted aryl,
 c) unsubstituted or substituted heterocycle,
 d) unsubstituted or substituted cycloalkyl, and
 e) $C_1$–$C_6$ alkyl substituted with hydrogen or an unsubstituted or substituted group selected from aryl, heterocycle and cycloalkyl;

$R^{7b}$ is selected from
 a) hydrogen,
 b) unsubstituted or substituted aryl,
 c) unsubstituted or substituted heterocycle,
 d) unsubstituted or substituted cycloalkyl,
 e) $C_1$–$C_6$ alkyl substituted with hydrogen or an unsubstituted or substituted group selected from aryl, heterocycle and cycloalkyl,
 f) a carbonyl group which is bonded to an unsubstituted or substituted group selected from aryl, heterocycle, cycloalkyl and $C_1$–$C_6$ alkyl substituted with hydrogen or an unsubstituted or substituted group selected from aryl, heterocycle and cycloalkyl, and
 g) a sulfonyl group which is bonded to an unsubstituted or substituted group selected from aryl, heterocycle, cycloalkyl and $C_1$–$C_6$ alkyl substituted with hydrogen or an unsubstituted or substituted group selected from aryl, heterocycle and cycloalkyl;

$R^8$ is independently selected from hydrogen, $C_1$–$C_6$ alkyl and aryl;
$R^9$ is independently selected from $C_1$–$C_6$ alkyl and aryl;
$R^{10}$ is independently selected from hydrogen and $C_1$–$C_6$ alkyl;
$R^{11}$ is independently selected from $C^1$–$C_6$ alkyl;
$Z^1$ and $Z^2$ are independently $H_2$ or O, provided that $Z^1$ is not O when X-Y is —C(O)N($R^{7a}$)—;

m is 0, 1 or 2;
s is 4 or 5; and
t is 3, 4 or 5;

or the pharmaceutically acceptable salts thereof.

In a third embodiment of this invention, the inhibitors of farnesyl transferase are illustrated by the formula III:

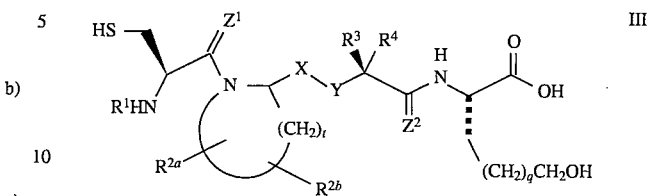

III wherein:
$R^1$ is selected from:
 a) hydrogen,
 b) $R^8S(O)_2$-, $R^8C(O)$-, $(R^8)_2NC(O)$- or $R^9OC(O)$-, and
 c) $C_1$–$C_6$ alkyl unsubstituted or substituted by aryl, heterocyclic, cycloalkyl, alkenyl, alkynyl, $R^8O$-, $R^8S(O)_m$-, $R^8C(O)NR^8$-, CN, $(R^8)_2N$-C($NR^8$)-, $R^8C(O)$-, $R^8OC(O)$-, $N_3$, —$N(R^8)_2$, or $R^9OC(O)NR^8$-;

$R^{2a}$ and $R^{2b}$ are independently selected from:
 a) hydrogen,
 b) $C_1$–$C_6$ alkyl unsubstituted or substituted by alkenyl, $R^8O$-, $R^8S(O)_m$-, $R^8C(O)NR^8$-, CN, $(R^8)_2N$-C($NR^8$)-, $R^8C(O)$-, $R^8OC(O)$-, $N_3$, —$N(R^8)^2$, or $R^9OC(O)NR^8$-,
 c) aryl, heterocycle, cycloalkyl, alkenyl, $R^8O$-, $R^8S(O)_m$-, $R^8C(O)NR^8$-, CN, $NO_2$, $(R^8)_2N$- C($NR_8$)-, $R^8C(O)$-, $R^8OC(O)$-, $N_3$, —$N(R^8)_2$, or $R^9OC(O)NR^8$-, and
 d) $C_1$–$C_6$ alkyl substituted with an unsubstituted or substituted group selected from aryl, heterocyclic and $C_3$–$C_{10}$ cycloalkyl;

$R_3$ and $R_4$ are independently selected from:
 a) a side chain of a naturally occurring amino acid,
 b) an oxidized form of a side chain of a naturally occurring amino acid which is:
  i) methionine sulfoxide, or
  ii) methionine sulfone, and
 c) substituted or unsubstituted $C_1$–$C_{20}$ alkyl, $C_2$–$C_{20}$ alkenyl, $C_3$–$C_{10}$ cycloalkyl, aryl or heterocyclic group, wherein the substituent is selected from F, Cl, Br, $N(R^8)_2$, $NO_2$, $R_8O$-, $R^8S(O)_m$-, $R_8C(O)NR_8$-, CN, $(R_8)_2N$-C($NR_8$)-, $R^8C(O)$-, $R^8OC(O)$-, $N_3$, —$N(R^8)_2$, $R^9OC(O)NR^8$- and $C_1$–$C_{20}$ alkyl, and
 d) $C_1$–$C_6$ alkyl substituted with an unsubstituted or substituted group selected from aryl, heterocyclic and $C_3$–$C_{10}$ cycloalkyl; or $R^3$ and $R^4$ are combined to form —$(CH_2)_s$—;

X-Y is

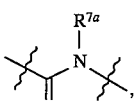 a)

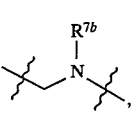 b)

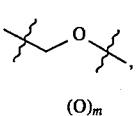 c)

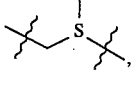 d)

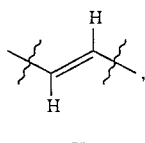

or

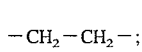

$R^{7a}$ is selected from
a) hydrogen,
b) unsubstituted or substituted aryl,
c) unsubstituted or substituted heterocycle,
d) unsubstituted or substituted cycloalkyl, and
e) $C_1-C_6$ alkyl substituted with hydrogen or an unsubstituted or substituted group selected from aryl, heterocycle and cycloalkyl;

$R^{7b}$ is selected from
a) hydrogen,
b) unsubstituted or substituted aryl,
c) unsubstituted or substituted heterocycle,
d) unsubstituted or substituted cycloalkyl,
e) $C_1-C_6$ alkyl substituted with hydrogen or an unsubstituted or substituted group selected from aryl, heterocycle and cycloalkyl,
f) a carbonyl group which is bonded to an unsubstituted or substituted group selected from aryl, heterocycle, cycloalkyl and $C_1-C_6$ alkyl substituted with hydrogen or an unsubstituted or substituted group selected from aryl, heterocycle and cycloalkyl, and
g) a sulfonyl group which is bonded to an unsubstituted or substituted group selected from aryl, heterocycle, cycloalkyl and $C_1-C_6$ alkyl substituted with hydrogen or an unsubstituted or substituted group selected from aryl, heterocycle and cycloalkyl;

$R_8$ is independently selected from hydrogen, $C_1-C_6$ alkyl and aryl;
$R_9$ is independently selected from $C_1-C_6$ alkyl and aryl;
$Z^1$ and $Z^2$ are independently $H_2$ or O, provided that $Z^1$ is not O when X-Y is -C(O)N($R^{7a}$);

m is 0, 1 or 2;
q is 0, 1 or 2;
s is 4 or 5; and
t is 3, 4 or 5;
or the pharmaceutically acceptable salts thereof.

In a fourth embodiment of this invention the prodrugs of compounds of formula III are illustrated by the formula IV:

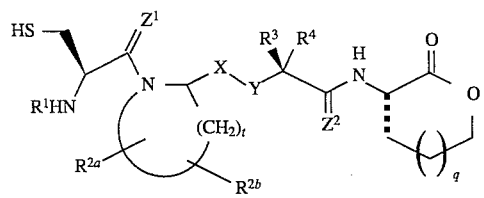

wherein:
$R^1$ is selected from:
a) hydrogen,
b) $R^8S(O)_2-$, $R^8C(O)-$, $(R^8)_2NC(O)-$ or $R^9OC(O)-$, and
c) $C_1-C_6$ alkyl unsubstituted or substituted by aryl, heterocyclic, cycloalkyl, alkenyl, alkynyl, $R^8O-$, $R^8S(O)_m-$, $R^8C(O)NR^8-$, CN, $(R^8)_2N-C(NR^8)-$, $R^8C(O)-$, $R^8OC(O)-$, $N_3$, $-N(R^8)_2$, or $R^9OC(O)NR^8-$;

$R^{2a}$ and $R^{2b}$ are independently selected from:
a) hydrogen,
b) $C_1-C_6$ alkyl unsubstituted or substituted by alkenyl, $R^8O-$, $R^8S(O)_m-$, $R^8C(O)NR^8-$, CN, $(R^8)_2N-C(NR^8)-$, $R^8C(O)-$, $R^8OC(O)-$, $N_3$, $-N(R^8)_2$, or $R^9OC(O)NR^8-$,
c) aryl, heterocycle, cycloalkyl, alkenyl, $R^8O-$, $R^8S(O)_m-$, $R^8C(O)NR^8-$, CN, $NO_2$, $(R^8)_2N-C(NR^8)-$, $R^8C(O)-$, $R^8OC(O)-$, $N_3$, $-N(R^8)_2$, or $R^9OC(O)NR^8-$, and
d) $C_1-C_6$ alkyl substituted with an unsubstituted or substituted group selected from aryl, heterocyclic and $C_3-C_{10}$ cycloalkyl;

$R^3$ and $R^4$ are independently selected from:
a) a side chain of a naturally occurring amino acid,
b) an oxidized form of a side chain of a naturally occurring amino acid which is:
i) methionine sulfoxide, or
ii) methionine sulfone, and
c) substituted or unsubstituted $C_1-C_{20}$ alkyl, $C_2-C_{20}$ alkenyl, $C_3-C_{10}$ cycloalkyl, aryl or heterocyclic group, wherein the substituent is selected from F, Cl, Br, $N(R^8)_2$, $NO_2$, $R^8O-$, $R^8S(O)_m-$, $R^8C(O)NR^8-$, CN, $(R^8)_2N-C(NR^8)-$, $R^8C(O)-$, $R^8OC(O)-$, $N_3$, $-N(R^8)_2$, $R^9OC(O)NR-$ and $C_1-C_{20}$ alkyl, and
d) $C_1-C_6$ alkyl substituted with an unsubstituted or substituted group selected from aryl, heterocyclic and $C_3-C_{10}$ cycloalkyl;or
$R^3$ and $R^4$ are combined to form $-(CH_2)_s-$;
X-Y is

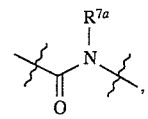  a)

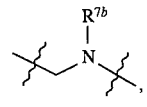  b)

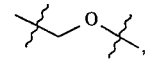  c)

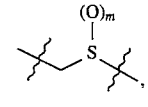  d)

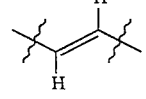  e)

or

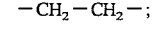  f)

$R^{7a}$ is selected from
a) hydrogen,
b) unsubstituted or substituted aryl,
c) unsubstituted or substituted heterocycle,
d) unsubstituted or substituted cycloalkyl, and
e) $C_1-C_6$ alkyl substituted with hydrogen or an unsubstituted or substituted group selected from aryl, heterocycle and cycloalkyl;

$R^{7b}$ is selected from
a) hydrogen,

11 b) unsubstituted or substituted aryl, c) unsubstituted or substituted heterocycle, d) unsubstituted or substituted cycloalkyl, e) $C_1$–$C_6$ alkyl substituted with hydrogen or an unsubstituted or substituted group selected from aryl, heterocycle and cycloalkyl, f) a carbonyl group which is bonded to an unsubstituted or substituted group selected from aryl, heterocycle, cycloalkyl and $C_1$–$C_6$ alkyl substituted with hydrogen or an unsubstituted or substituted group selected from aryl, heterocycle and cycloalkyl, and g) a sulfonyl group which is bonded to an unsubstituted or substituted group selected from aryl, heterocycle, cycloalkyl and $C_1$–$C_6$ alkyl substituted with hydrogen or an unsubstituted or substituted group selected from aryl, heterocycle and cycloalkyl;

$R^8$ is independently selected from hydrogen, $C_1$–$C_6$ alkyl and aryl;

$R^9$ is independently selected from $C_1$–$C_6$ alkyl and aryl;

$Z^1$ and $Z^2$ are independently $H_2$ or O, provided that Z1 is not O when

X-Y is —C(O)N($R^{7a}$)-;

m is 0, 1 or 2;

q is 0, 1 or 2;

s is 4 or 5; and t is 3, 4 or 5;

or the pharmaceutically acceptable salts thereof.

In a more preferred embodiment of this invention, the Ras farnesyl transferase inhibitors are illustrated by the formula I:

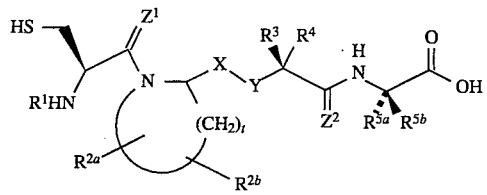

wherein:

$R^1$ is selected from:

a) hydrogen, b) $R^8S(O)_2$-, $R^8C(O)$-, $(R^8)_2NC(O)$- or $R^9OC(O)$-, and c) $C_1$–$C_6$ alkyl unsubstituted or substituted by aryl, heterocyclic, cycloalkyl, alkenyl, alkynyl, $R^8O$-, $R^8S(O)_m$-, $R^8C(O)NR^8$-, CN, $(R^8)_2$N-C($NR^8$)-, $R^8C(O)$-, $R^8OC(O)$-, $N_3$, —N($R^8$)$_2$, or $R^9OC(O)NR^8$-;

$R^{2a}$ is selected from:

a) a side chain of a naturally occurring amino acid, wherein the amino acid is selected from alanine, leucine, isoleucine, norleucine, valine and norvaline:

b) substituted or unsubstituted $C_1$–$C_{10}$ alkyl, $C_2$–$C_{10}$ alkenyl, $C_3$–$C_{10}$ cycloalkyl, aryl or heterocyclic group, wherein the substituent is selected from F, Cl, Br, NO$_2$, $R^8O$-, $R^8S(O)_m$-, $R^8C(O)^8$-, CN, $(R^8)_2$N- C($NR^8$)-, $R^8C(O)$-, $R^8OC(O)$-, $N_3$, —N($R^8$)$_2$, $R^9OC(O)NR^8$- and $C_1$–$C_{20}$ alkyl, and c) $C_1$–$C_6$ alkyl substituted with an unsubstituted or substituted group selected from aryl, heterocyclic and $C_3$–$C_{10}$ cycloalkyl; and $R^{2b}$ is selected from hydrogen and $C_1$–$C_6$ alkyl;

$R^3$ and $R^4$ are independently selected frown:

a) a side chain of a naturally occurring amino acid, b) an oxidized form of a side chain of a naturally occurring amino acid which is:

12 i) methionine sulfoxide, or ii) methionine sulfone, c) substituted or unsubstituted $C_1$–$C_{10}$ alkyl, $C_2$–$C_{10}$ alkenyl, $C_3$–$C_{10}$ cycloalkyl, aryl or heterocycle group, wherein the substituent is selected from F, Cl, Br, NO$_2$, $R^8O$-, $R^8S(O)_m$-, $R_8C(O)NR^8$-, CN, $(R^8)_2$N-C($NR^8$)-, $R^8C(O)$-, $R^8OC(O)$-, $N_3$, —N($R^8$)$_2$, $R^9OC(O)NR^8$- and $C_1$–$C_{20}$ alkyl, and d) $C_1$–$C_6$ alkyl substituted with an unsubstituted or substituted group selected from aryl, heterocyclic and $C_3$–$C_{10}$ cycloalkyl;

$R^{5a}$ is selected from:

a) a side chain of a naturally occurring amino acid, wherein the amino acid is selected from methionine and glutamine, b) an oxidized form of a side chain of a naturally occurring amino acid which is:

i) methionine sulfoxide, or ii) methionine sulfone, c) substituted or unsubstituted $C_1$–$C_{10}$ alkyl, $C_2$–$C_{10}$ alkenyl, $C_3$–$C_{10}$ cycloalkyl, aryl or heterocyclic group, wherein the substituent is selected from F, Cl, Br, NO$_2$, $R^8O$-, $R^8S(O)_m$-, $R^8C(O)NR^8$-, CN, $(R^8)_2$N-C($NR^8$)-, $R^8C(O)$-, $R^8OC(O)$-, $N_3$, —N($R^8$)$_2$, $R^9OC(O)NR^8$- and $C_1$–$C_{20}$ alkyl, and d) $C_1$–$C_6$ alkyl substituted with an unsubstituted or substituted group selected from aryl, heterocyclic and $C_3$–$C_{10}$ cycloalkyl;

$R^5b$ is selected from:

a) hydrogen, and b) $C^1$–$C_3$ alkyl;

X-Y is

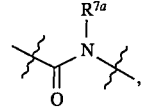 a)

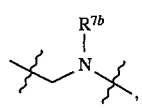 b)

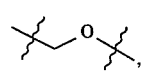 c)

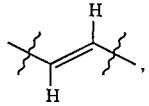 d)

or $-CH_2-CH_2-;$ e)

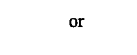

$R^{7a}$ is selected from a) hydrogen, b) unsubstituted or substituted aryl, c) unsubstituted or substituted heterocycle, d) unsubstituted or substituted cycloalkyl, and e) $C_1$–$C_6$ alkyl substituted with hydrogen or an unsubstituted or substituted group selected from aryl, heterocycle and cycloalkyl;

wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^{7b}$ is selected from

13 a) hydrogen,
b) unsubstituted or substituted aryl,
c) unsubstituted or substituted heterocycle,
d) unsubstituted or substituted cycloalkyl,
e) $C_1$–$C_6$ alkyl substituted with hydrogen or an unsubstituted or substituted group selected from aryl, heterocycle and cycloalkyl,
f) a carbonyl group which is bonded to an unsubstituted or substituted group selected from aryl, heterocycle, cycloalkyl and $C_1$–$C_6$ alkyl substituted with hydrogen or an unsubstituted or substituted group selected from aryl, heterocycle and cycloalkyl, and
g) a sulfonyl group which is bonded to an unsubstituted or substituted group selected from aryl, heterocycle, cycloalkyl and $C_1$–$C_6$ alkyl substituted with hydrogen or an unsubstituted or substituted group selected from aryl, heterocycle and cycloalkyl;
   wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^8$ is independently selected from hydrogen, $C_1$–$C_6$ alkyl and aryl;
$R^9$ is independently selected from $C_1$–$C_6$ alkyl and aryl;
$Z^1$ and $Z^2$ are independently $H_2$ or O, provided that $Z^1$ is not O when X-Y is —C(O)N($R^{7a}$)-;

m is 0, 1 or 2; and
t is 3, 4 or 5;
or the pharmaceutically acceptable salts thereof.

In a second more preferred embodiment of this invention, the prodrugs of the preferred compounds of formula I are illustrated by the formula II:

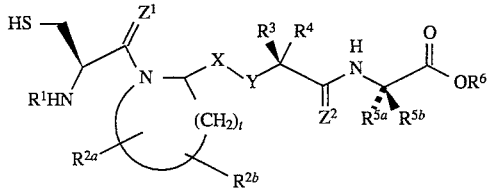

wherein:
$R^1$ is selected from:
a) hydrogen,
b) $R^8S(O)_2$-, $R^8C(O)$-, $(R^8)_2NC(O)$- or $R^9OC(O)$-, and
c) $C_1$–$C_6$ alkyl unsubstituted or substituted by aryl, heterocyclic, cycloalkyl, alkenyl, alkynyl, $R^8O$-, CN, $R^8S(O)_m$-, $R^8C(O)NR^8$-, $(R^8)_2N$-$C(NR^8)$-, $R^8C(O)$-, $R^8OC(O)$-, $N_3$, —N($R^8)_2$, or $R^9OC(O)NR^8$-;

$R^{2a}$ is selected from:
a) a side chain of a naturally occurring amino acid, wherein the amino acid is selected from alanine, leucine, isoleucine, norleucine, valine and norvaline; and
b) substituted or unsubstituted $C_1$–$C_{10}$ alkyl, $C_2$–$C_{10}$ alkenyl, $C_3$–$C_{10}$ cycloalkyl, aryl or heterocyclic group, wherein the substituent is selected from F, Cl, Br, $NO_2$, $R^8O$-, $R^8S(O)_m$, $R^8C(O)NR^8$-, CN, $(R^8)_2N$-$C(NR^8)$-, $R^8C(O)$-, $R^8OC(O)$-, $N_3$, —N($R^8)2$, $R^9OC(O)NR^8$- and $C_1$–$C_{20}$ alkyl, and
c) $C_1$–$C_6$ alkyl substituted with an unsubstituted or substituted group selected from aryl, heterocyclic and $C_3$–$C_{10}$ cycloalkyl;

$R^{2b}$ is selected from hydrogen and $C_1$–$C_6$ alkyl;

14

$R^3$ and $R^4$ are independently selected from:
a) a side chain of a naturally occurring amino acid,
b) an oxidized form of a side chain of a naturally occurring amino acid which is:
   i) methionine sulfoxide, or
   ii) methionine sulfone,
c) substituted or unsubstituted $C_1$–$C_{10}$ alkyl, $C_2$–$C_{10}$ alkenyl, $C_3$–$C_{10}$ cycloalkyl, aryl or heterocycle group, wherein the substituent is selected from F, Cl, Br, $NO_2$, $R^8O$-, $R^8S(O)_m$, $R^8C(O)NR^8$-, CN, $(R^8)_2N$-$C(NR^8)$-, $R^8C(O)$-, $R^8OC(O)$-, $N_3$, —N($R^8)_2$, $R^9OC(O)NR^8$-, $C_1$–$C_{20}$ alkyl, or heterocycle:

$R^{5a}$ is selected from:
a) a side chain of a naturally occurring amino acid, wherein the amino acid is selected from methionine and glutamine,
b) an oxidized form of a side chain of a naturally occurring amino acid which is:
   i) methionine sulfoxide, or
   ii) methionine sulfone, and
c) substituted or unsubstituted $C_1$–$C_{10}$ alkyl, $C_2$–$C_{10}$ alkenyl, $C_3$–$C_{10}$ cycloalkyl, aryl or heterocyclic group, wherein the substituent is selected from F, Cl, Br, $NO_2$, $R^8O$-, $R^8S(O)_m$, $R^8C(O)NR^8$-, CN, $(R^8)_2N$-$C(NR^8)$-, $R^8C(O)$-, $R^8OC(O)$-, $N_3$, —N($R^8)_2$, $R^9OC(O)NR^8$- and $C_1$–$C_{20}$ alkyl, and
d) $C_1$–$C_6$ alkyl substituted with an unsubstituted or substituted group selected from aryl, heterocyclic and $C_3$–$C_{10}$ cycloalkyl;

$R^{5b}$ is selected from:
a) hydrogen, and
b) $C_1$–$C_3$ alkyl;

X-Y is

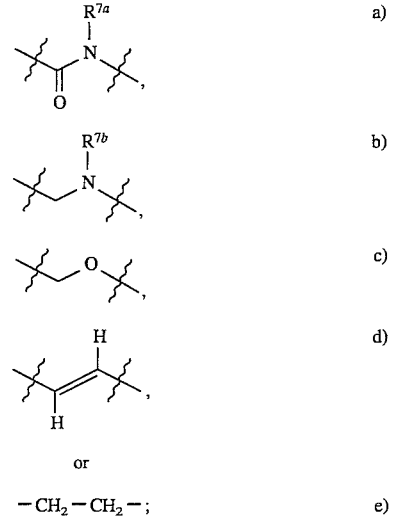

a)

b)

c)

d)

or

—$CH_2$—$CH_2$—;     e)

$R^6$ is
a) substituted or unsubstituted $C_1$–$C_8$ alkyl, wherein the substituent on the alkyl is selected from:
   1) aryl.
   2) heterocycle,
   3) —N($R^9)2$,
   4) —$OR^8$, or b)

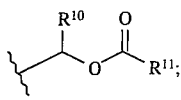

$R^{7a}$ is selected from
a) hydrogen,
b) unsubstituted or substituted aryl,
c) unsubstituted or substituted heterocycle,
d) unsubstituted or substituted cycloalkyl, and
e) $C_1$–$C_6$ alkyl substituted with hydrogen or an unsubstituted or substituted group selected from aryl, heterocycle and cycloalkyl;
wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^{7b}$ is selected from
a) hydrogen,
b) unsubstituted or substituted aryl,
c) unsubstituted or substituted heterocycle,
d) unsubstituted or substituted cycloalkyl,
e) $C_1$–$C_6$ alkyl substituted with hydrogen or an unsubstituted or substituted group selected from aryl, heterocycle and cycloalkyl,
f) a carbonyl group which is bonded to an unsubstituted or substituted group selected from aryl, heterocycle, cycloalkyl and $C_1$–$C_6$ alkyl substituted with hydrogen or an unsubstituted or substituted group selected from aryl, heterocycle and cycloalkyl, and
g) a sulfonyl group which is bonded to an unsubstituted or substituted group selected from aryl, heterocycle, cycloalkyl and $C_1$–$C_6$ alkyl substituted with hydrogen or an unsubstituted or substituted group selected from aryl, heterocycle and cycloalkyl;
wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^8$ is independently selected from hydrogen, $C_1$–$C_6$ alkyl and aryl;
$R^9$ is independently selected from $C_1$–$C_6$ alkyl and aryl;
$R^{10}$ is independently selected from hydrogen and $C_1$–$C_6$ alkyl;
$R^{11}$ is 1,1-dimethylethyl;
$Z^1$ and $Z^2$ are independently $H_2$ or O, provided that $Z^1$ is not O when X-Y is —C(O)N($R^{7a}$)—;

m is 0, 1 or 2; and
t is 3, 4 or 5;
or the pharmaceutically acceptable salts thereof.

In a third more preferred embodiment of this invention, the inhibitors of farnesyl transferase are illustrated by the formula III:

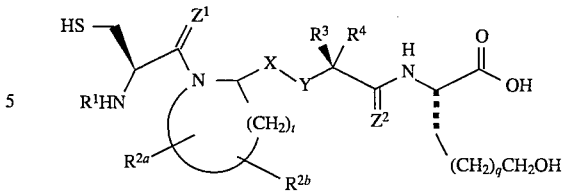

wherein:
$R^1$ is selected from:
a) hydrogen,
b) $R^8S(O)_2$—, $R^8C(O)$—, $(R^8)_2NC(O)$— or $R^9OC(O)$—, and
c) $C_1$–$C_6$ alkyl unsubstituted or substituted by aryl, heterocyclic, cycloalkyl, alkenyl, alkynyl, $R^8O$—, $R^8S(O)_m$, $R^8C(O)NR^8$—, CN, $(R^8)_2N$-$C(NR^8)$—, $R^8C(O)$—, $R^8OC(O)$—, $N_3$, —$N(R^8)_2$, or $R^9OC(O)NR^8$—;

$R^{2a}$ is selected from:
a) a side chain of a naturally occurring amino acid, wherein the amino acid is selected from alanine, leucine, isoleucine, norleucine, valine and norvaline; and
b) substituted or unsubstituted $C_1$–$C_{10}$ alkyl, $C_2$–$C_{10}$ alkenyl, $C_3$–$C_{10}$ cycloalkyl, aryl or heterocyclic group, wherein the substituent is selected from F, Cl, Br, $NO_2$, $R^8O$—, $R^8S(O)_m$, $R^8C(O)NR^8$—, CN, $(R^8)_2N$-$C(NR^8)$—, $R^8C(O)$—, $R^8OC(O)$—, $N_3$, —$N(R^8)_2$, $R^9OC(O)NR^8$— and $C_1$–$C_{20}$ alkyl, and
c) $C_1$–$C_6$ alkyl substituted with an unsubstituted or substituted group selected from aryl, heterocyclic and $C_3$–$C_{10}$ cycloalkyl;

$R^{2b}$ is selected from hydrogen and $C_1$–$C_6$ alkyl;
$R^3$ and $R^4$ are independently selected from:
a) a side chain of a naturally occurring amino acid,
b) an oxidized form of a side chain of a naturally occurring amino acid which is:
i) methionine sulfoxide, or
ii) methionine sulfone,
c) substituted or unsubstituted $C_1$–$C_{10}$ alkyl, $C_2$–$C_{10}$ alkenyl, $C_3$–$C_{10}$ cycloalkyl, aryl or heterocycle group, wherein the substituent is selected from F, Cl, Br, $NO_2$, $R^8O$—, $R^8S(O)_m$, $R^8C(O)NR^8$—, CN, $(R^8)_2N$-$C(NR^8)$—, $R^8C(O)$—, $R^8OC(O)$—, $N_3$, —$N(R^8)_2$, $R^9OC(O)NR^8$— and $C_1$–$C_{20}$ alkyl, and
d) $C_1$–$C_6$ alkyl substituted with an unsubstituted or substituted group selected from aryl, heterocyclic and $C_3$–$C_{10}$ cycloalkyl;

X-Y is a) 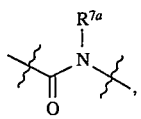

b) 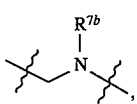

c) 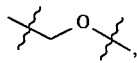

d) 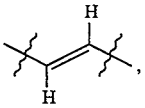

-continued or $-CH_2-CH_2-$;   e)

$R^{7a}$ is selected from
a) hydrogen,
b) unsubstituted or substituted aryl,
c) unsubstituted or substituted heterocycle,
d) unsubstituted or substituted cycloalkyl, and
e) $C_1-C_6$ alkyl substituted with hydrogen or an unsubstituted or substituted group selected from aryl, heterocycle and cycloalkyl;
wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^{7b}$ is selected from
a) hydrogen,
b) unsubstituted or substituted aryl,
c) unsubstituted or substituted heterocycle,
d) unsubstituted or substituted cycloalkyl,
e) $C_1-C_6$ alkyl substituted with hydrogen or an unsubstituted or substituted group selected from aryl, heterocycle and cycloalkyl,
f) a carbonyl group which is bonded to an unsubstituted or substituted group selected from aryl, heterocycle, cycloalkyl and $C_1-C_6$ alkyl substituted with hydrogen or an unsubstituted or substituted group selected from aryl, heterocycle and cycloalkyl, and
g) a sulfonyl group which is bonded to an unsubstituted or substituted group selected from aryl, heterocycle, cycloalkyl and $C_1-C_6$ alkyl substituted with hydrogen or an unsubstituted or substituted group selected from aryl, heterocycle and cycloalkyl;
wherein heterocycle is selected from pyrrolidinyl, imidazolyl, pyridmyl, thiazolyl, pyridonyl, 2-oxopiperidinyl, indolyl, quinolinyl, isoquinolinyl, and thienyl;

$R^8$ is independently selected from hydrogen, $C_1-C_6$ alkyl and aryl;
$R^9$ is independently selected from $C_1-C_6$ alkyl and aryl;
$Z^1$ and $Z^2$ are independently $H_2$ or O, provided that $Z^1$ is not O when X-Y is $-C(O)N(R^{7a})-$;

m is 0, 1 or 2;
q is 0, 1 or 2; and
t is 3, 4 or 5;
or the pharmaceutically acceptable salts thereof.

In a fourth more preferred embodiment of this invention, the prodrugs of the preferred compounds of formula III are illustrated by the formula IV:

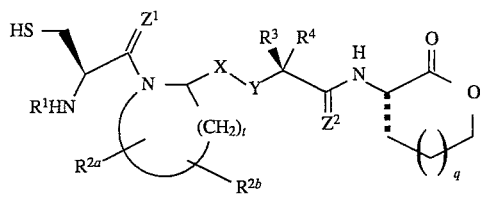

IV wherein:
$R^1$ is selected from:
a) hydrogen,
b) $R^8S(O)_2-$, $R^8C(O)-$, $(R^8)_2NC(O)-$ or $R^9OC(O)-$, and
c) $C_1-C_6$ alkyl unsubstituted or substituted by aryl, heterocyclic, cycloalkyl, alkenyl, alkynyl, $R^8O-$, $R^8S(O)_m$, $R^8C(O)NR^8-$, CN, $(R^8)_2N-C(NR^8)-$, $R^8C(O)-$, $R^8OC(O)-$, $N_3$, $-N(R^8)_2$, or $R^9OC(O)NR^8-$;

$R^{2a}$ is selected from:
a) a side chain of a naturally occurring amino acid, wherein the amino acid is selected from alanine, leucine, isoleucine, norleucine, valine and norvaline;
b) substituted or unsubstituted $C_1-C_{10}$ alkyl, $C_2-C_{10}$ alkenyl, $C_3-C_{10}$ cycloalkyl, aryl or heterocyclic group, wherein the substituent is selected from F, Cl, Br, $NO_2$, $R^8O-$, $R^8S(O)_m-$, $R^8C(O)NR^8-$, CN, $(R^8)_2N-C(NR^8)-$, $R^8C(O)-$, $R^8OC(O)-$, $N_3$, $-N(R^8)_2$, $R^9OC(O)NR^8-$ and $C_1-C_{20}$ alkyl, and
c) $C_1-C_6$ alkyl substituted with an unsubstituted or substituted group selected from aryl, heterocyclic and $C_3-C_{10}$ cycloalkyl;

$R^{2b}$ is selected from hydrogen and $C_1-C_6$ alkyl;
R3 and R4 are independently selected from:
a) a side chain of a naturally occurring amino acid,
b) an oxidized form of a side chain of a naturally occurring amino acid which is:
i) methionine sulfoxide, or
ii) methionine sulfone,
c) substituted or unsubstituted $C_1-C_{10}$ alkyl, $C_2-C_{10}$ alkenyl, $C_3-C_{10}$ cycloalkyl, aryl or heterocycle group, wherein the substituent is selected from F, Cl, Br, $NO_2$, $R^8O-$, $R^8S(O)_m$, $R^8C(O)NR^8-$, CN, $(R^8)_2N-C(NR^8)-$, $R^8C(O)-$, $R^8OC(O)-$, $N_3$, $-N(R^8)_2$, $R^9OC(O)NR^8-$ and $C_1-C_{20}$ alkyl, and
d) $C_1-C_6$ alkyl substituted with an unsubstituted or substituted group selected from aryl, heterocyclic and $C_3-C_{10}$ cycloalkyl;

X-Y is

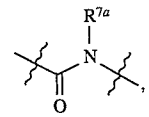   a)

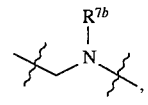   b)

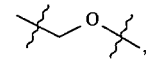   c)

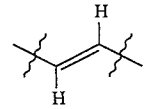   d)

or $-CH_2-CH_2-$;   e)

$R^{7a}$ is selected from
a) hydrogen,
b) unsubstituted or substituted aryl,
c) unsubstituted or substituted heterocycle,
d) unsubstituted or substituted cycloalkyl, and
e) $C_1-C_6$ alkyl substituted with hydrogen or an unsubstituted or substituted group selected from aryl, heterocycle and cycloalkyl;
wherein heterocycle is selected frown pyrrolidinyl, imidazolyl, pyridinyl, thiazolyl, pyridonyl, 2-oxopiperidinyl, indolyl, quinolinyl, isoquinolinyl, and thienyl;

$R^{7b}$ is selected from
a) hydrogen,
b) unsubstituted or substituted aryl,
c) unsubstituted or substituted heterocycle,
d) unsubstituted or substituted cycloalkyl,
e) $C_1$–$C_6$ alkyl substituted with hydrogen or an unsubstituted or substituted group selected from aryl, heterocycle and cycloalkyl,
f) a carbonyl group which is bonded to an unsubstituted or substituted group selected from aryl, heterocycle, cycloalkyl and $C_1$–$C_6$ alkyl substituted with hydrogen or an unsubstituted or substituted group selected from aryl, heterocycle and cycloalkyl, and
g) a sulfonyl group which is bonded to an unsubstituted or substituted group selected from aryl, heterocycle, cycloalkyl and $C_1$–$C_6$ alkyl substituted with hydrogen or an unsubstituted or substituted group selected from aryl, heterocycle and cycloalkyl;
wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^8$ is independently selected from hydrogen, $C_1$–$C_6$ alkyl and aryl;

$R^9$ is independently selected from $C_1$–$C_6$ alkyl and aryl;

$Z^1$ and $Z^2$ are independently $H_2$ or $O$, provided that $Z^1$ is not $O$ when X-Y is —C(O)N($R^{7a}$)-;

m is 0, 1 or 2;
q is 0, 1 or 2; and
t 3, 4 or 5;
or the pharmaceutically acceptable salts thereof.

The preferred compounds of this invention are as follows:
N-[1-(2(R)-amino-3-mercaptopropyl)-2(S)-pyrrolidinylmethyl]N-(1-naphthylmethyl)glycyl-methionine

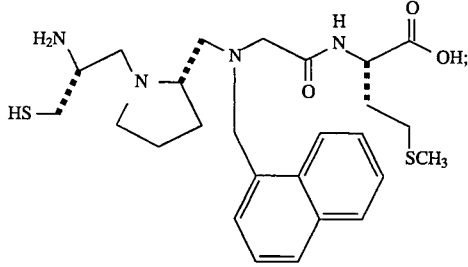

N-[1-(2(R)-amino-3-mercaptopropyl)-2(S)-pyrrolidinylmethyl]-N-(1-naphthylmethyl)glycyl-methionine methyl ester

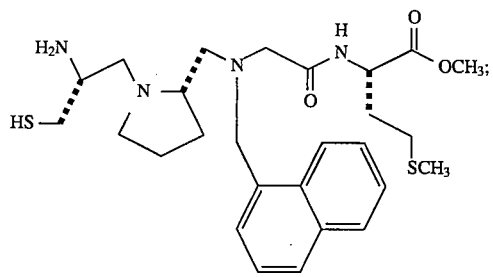

2(S)-[[1-[2(R)-Amino-3-mercapto]propyl]-2(S)-(pyrrolidinyl)-methyloxy]-3-phenylpropionyl-methionine

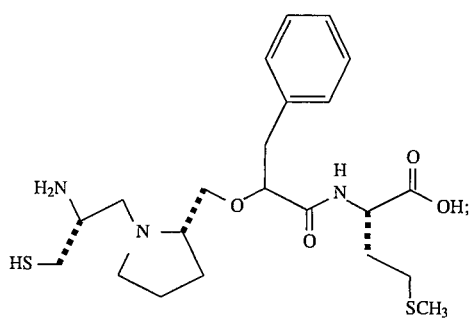

2(S)-[[1-[2(S)-Amino-3-mercapto]propyl]-2(S)-(pyrrolidinyl)methyloxy]-3-phenylpropionyl-methionine

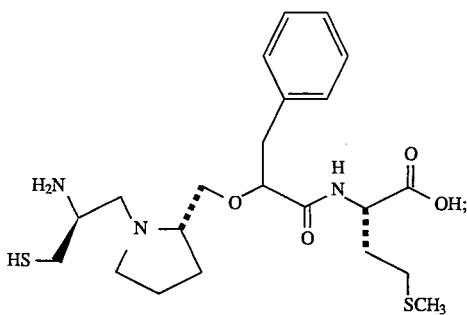

or the pharmaceutically acceptable salts thereof.

In the present invention, the amino acids which are disclosed are identified both by conventional 3 letter and single letter abbreviations as indicated below:

| | | |
|---|---|---|
| Alanine | Ala | A |
| Arginine | Arg | R |
| Asparagine | Asn | N |
| Aspartic acid | Asp | D |
| Asparagine or Aspartic acid | Asx | B |
| Cysteine | Cys | C |
| Glutamine | Gln | Q |
| Glutamic acid | Glu | E |
| Glutamine or Glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The compounds of the present invention may have asymmetric centers and occur as racemates, racemic mixtures, and as individual diastereomers, with all possible isomers, including optical isomers, being included in the present invention.

As used herein, "alkyl" is intended to include both branched and straight-chain saturated aliphatic hydrocarbon groups having the specified number of carbon atoms.

As used herein, "cycloalkyl" is intended to include non-aromatic cyclic hydrocarbon groups having the specified number of carbon atoms. Examples of cycloalkyl groups include cyclopropyl, cyclobutyl, cyclopentyl, cyclohexyl and the like.

"Alkenyl" groups include those groups having the specified number of carbon atoms and having one or several double bonds. Examples of alkenyl groups include vinyl, allyl, isopropenyl, pentenyl, hexenyl, heptenyl, cyclopropenyl, cyclobutenyl, cyclopentenyl, cyclohexenyl, 1-propenyl, 2-butenyl, 2-methyl-2-butenyl, isoprenyl, farnesyl, geranyl, geranylgeranyl and the like.

As used herein. "aryl" is intended to include any stable monocyclic, bicyclic or tricyclic carbon ring(s) of up to 7 members in each ring, wherein at least one ring is aromatic. Examples of aryl groups include phenyl, naphthyl, anthracenyl, biphenyl, tetrahydronaphthyl, indanyl, phenanthrenyl and the like.

The term heterocycle or heterocyclic, as used herein, represents a stable 5- to 7-membered monocyclic or stable 8- to 11-membered bicyclic or stable 11–15 membered tricyclic heterocycle ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydro-benzothienyl, dihydrobenzothiopyranyl, dihydrobenzothio-pyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, 2-oxopiperazinyl, 2-oxopiperidinyl, 2-oxopyrrolidinyl, piperidyl, piperazinyl, pyridyl, pyridyl N-oxide, pyridonyl, pyrazinyl, pyrazolidinyl, pyrazolyl, pyrimidinyl, pyrrolidinyl, pyrrolyl, quinazolinyl, quinolinyl, quinolinyl N-oxide, quinoxalinyl, tetrahydrofuryl, tetrahydroisoquinolinyl, tetrahydro-quinolinyl, thiamorpholinyl, thiamorpholinyl sulfoxide, thiazolyl, thiazolinyl, thienofuryl, thienothienyl, and thienyl.

As used herein, the terms "substituted aryl", "substituted heterocycle" and "substituted cycloalkyl" are intended to include cyclic group which is substituted with 1 or 2 substitutents selected from the group which includes but is not limited to F, Cl, Br, CF$_3$, NH$_2$, N(C$_1$–C$_6$ alkyl)2, NO$_2$, CN, (C$_1$–C$_6$ alkyl)O-, —OH, (C$_1$–C$_6$ alkyl)S(O)$_m$, (C$_1$–C$_6$ alkyl)C(O)NH-, H$_2$N-C(NH)-, (C$_1$–C$_6$ alkyl)C(O)-, (C$_1$–C$_6$ alkyl)OC(O)-, N$_3$, (C$_1$–C$_6$ alkyl)OC(O)NH- and C$_1$–C$_{20}$ alkyl.

The following structure:

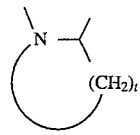

represents a cyclic amine moiety having 5 or 6 members in the ring, such a cyclic amine which may be optionally fused to a phenyl or cyclohexyl ring. Examples of such a cyclic amine moiety include, but are not limited to, the following specific structures:

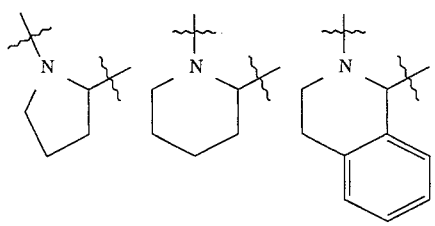

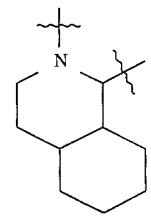

It is also understood that substitution on the cyclic amine moiety by $R^{2a}$ and $R^{2b}$ may be on different carbon atoms or on the same carbon atom.

When $R^3$ and $R^4$ are combined to form —(CH$_2$)$_s$—, cyclic moieties are formed. Examples of such cyclic moieties include, but are not limited to:

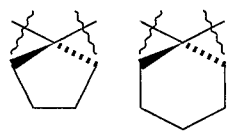

When $R^{5a}$ and $R^{5b}$ are combined to form —(CH$_2$)$_s$-, cyclic moieties as described hereinabove for $R^3$ and $R^4$ are formed. In addition, such cyclic moieties may optionally include a heteroatom(s). Examples of such heteroatom-containing cyclic moieties include, but are not limited to:

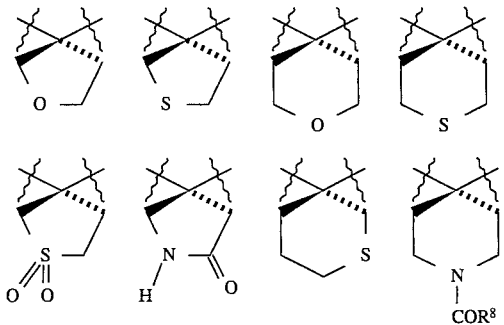

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenyl-acetic, glutamic, benzoic, salicylic, sulfanilic, 2-acetoxy-benzoic, fumaric, toluenesulfonic, methanesulfonic, ethane disulfonic. oxalic, isethionic, trifluoroacetic and the like.

It is intended that the definition of any substituent or variable (e.g., $R^8$, Z, n, etc.) at a particular location in a molecule be independent of its definitions elsewhere in that molecule. Thus, —N(R$^8$)$_2$ represents —NHH, —NHCH$_3$, —NHC₂H₅, etc. It is understood that substituents and substitution patterns on the compounds of the instant invention can be selected by one of ordinary skill in the art to provide compounds that are chemically stable and that can be readily synthesized by techniques known in the art as well as those methods set forth below.

The pharmaceutically acceptable salts of the compounds of this invention can be synthesized from the compounds of this invention which contain a basic moiety by conventional chemical methods. Generally, the salts are prepared by reacting the free base with stoichiometric amounts or with an excess of the desired salt-forming inorganic or organic acid in a suitable solvent or various combinations of solvents.

The compounds of the invention can be synthesized from their constituent amino acids by conventional peptide synthesis techniques, and the additional methods described below. Standard methods of peptide synthesis are disclosed, for example, in the following works: Schroeder et al., *"The Peptides"*, Vol. I, Academic Press 1965, or Bodanszky et al., *"Peptide Synthesis"*, Interscience Publishers, 1966, or McOmie (ed.) *"Protective Groups in Organic Chemistry"*, Plenum Press, 1973, or Barany et al., *"The Peptides: Analysis, Synthesis, Biology"* 2, Chapter 1, Academic Press, 1980, or Stewart et at., *"Solid Phase Peptide Synthesis"*, Second Edition, Pierce Chemical Company, 1984. The teachings of these works are hereby incorporated by reference.

Abbreviations used in the description of the chemistry and in the Examples that follow are:

| | |
|---|---|
| Ac₂O | Acetic anhydride; |
| Boc | t-Butoxycarbonyl; |
| DBU | 1,8-diazabicyclo[5.4.0]undec-7-ene; |
| DMAP | 4-Dimethylaminopyridine; |
| DME | 1,2-Dimethoxyethane; |
| DMF | Dimethylformamide; |
| EDC | 1-(3-dimethylaminopropyl)-3-ethyl-carbodiimide-hydrochloride; |
| HOBT | 1-Hydroxybenzotriazole hydrate; |
| Et₃N | Triethylamine; |
| EtOAc | Ethyl acetate; |
| FAB | Fast atom bombardment; |
| HOOBT | 3-Hydroxy-1,2,2-benzotriazin-4(3H)-one; |
| HPLC | High-performance liquid chromatography; |
| MCPBA | m-Chloroperoxybenzoic acid; |
| MsCl | Methanesulfonyl chloride; |
| NaHMDS | Sodium bis(trimethylsilyl)amide; |
| Py | Pyridine; |
| TFA | Trifluoroacetic acid; |
| THF | Tetrahydrofuran. |

Compounds of this invention are prepared by employing the reactions shown in the following Reaction Schemes A-J, in addition to other standard manipulations such as ester hydrolysis, cleavage of protecting groups, etc., as may be known in the literature or exemplified in the experimental procedures. Some key bond-forming and peptide modifying reactions are:

Reaction A. Amide bond formation and protecting group cleavage using standard solution or solid phase methodologies.

Reaction B. Preparation of a reduced peptide subunit by 1 reductive alkylation of an amine by an aldehyde using sodium cyanoborohydride or other reducing agents.

Reaction C. Alkylation of a reduced peptide subunit with an alkyl or aralkyl halide or, alternatively, reductive alkylation of a reduced peptide subunit with an aldehyde using sodium cyanoborohydride or other reducing agents.

Reaction D. Peptide bond formation and protecting group cleavage using standard solution or solid phase methodologies.

Reaction E. Preparation of a reduced subunit by borane reduction of the amide moiety.

Reaction Schemes A–E illustrate bond-forming and peptide modifying reactions incorporating acyclic peptide units. It is well understood that such reactions are equally useful when the —NHC(Rᴬ)— moiety of the reagents and compounds illustrated is replaced with the following moiety:

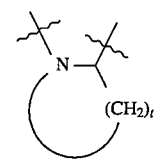

These reactions may be employed in a linear sequence to provide the compounds of tile invention or they may be used to synthesize fragments which are subsequently joined by the alkylation reactions described in tile Reaction Schemes.

REACTION SCHEME A
Reaction A. Coupling of residues to form an amide bond

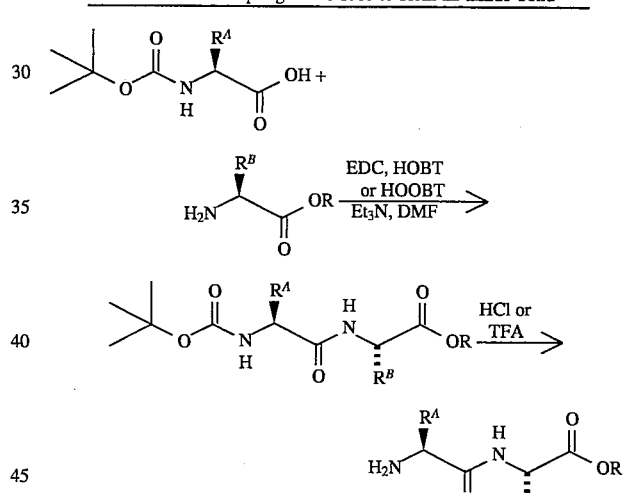

REACTION SCHEME B
Reaction B. Preparation of reduced peptide subunits by reductive alkylation

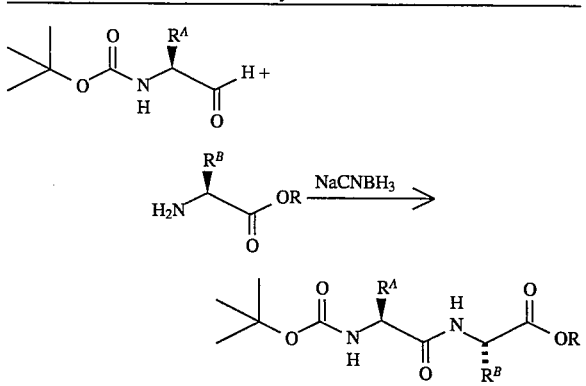

REACTION SCHEME C
Reaction C. Alkylation/reductive alkylation of reduced peptide subunits

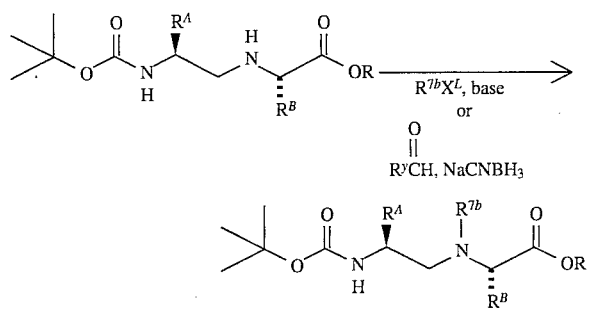

REACTION SCHEME D
Reaction D. Coupling of residues to form an amide bond

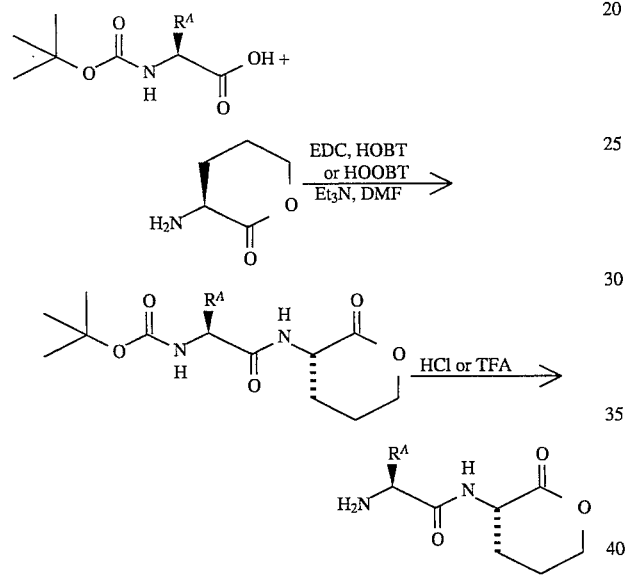

REACTION SCHEME E
Reaction E. Preparation of reduced dipeptides from peptides

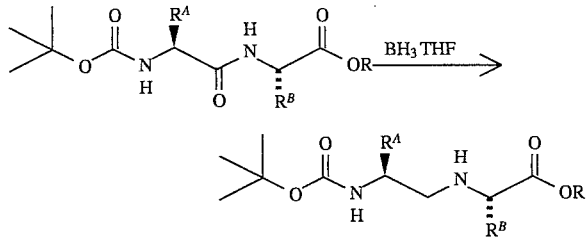

where $R^A$ and $R^B$ are $R^3$, $R^4$, $R^{5a}$ or $R^{5b}$ as previously defined; $X^L$ is a leaving group, e.g., Br-, I- or MsO-; and $R^Y$ is defined such that $R^{7b}$ is generated by the reductive alkylation process.

Certain compounds of this invention wherein X-Y is an ethenylene or ethylene unit are prepared by employing the reaction sequences shown in Reaction Schemes F and G. Reaction Scheme F outlines the preparation of the alkene isosteres utilizing standard manipulations such as Weinreb amide formation, Grignard reaction, acetylation, ozonolysis, Witrig reaction, ester hydrolysis, peptide coupling reaction, mesylation, cleavage of peptide protecting groups, reductive alkylation, etc., as may be shown in the literature or exemplified in the Experimental Procedure. For simplicity, substituents $R^{2a}$ and $R^{2b}$ on the cyclic amine moiety are not shown. It is, however, understood that the reactions illustrated are also applicable to appropriately substituted cyclic amine compounds. The key reactions are: stereoselective reduction of the Boc-amino-enone to the corresponding syn amino-alcohol (Scheme F, Step B, Part 1), and stereospecific boron trifluoride or zinc chloride activated organomagnesio, organo-lithio, or organo-zinc copper(I) cyanide $S_N2'$ displacement reaction (Scheme F, Step G). Through the use of optically pure N-Boc amino acids as starting material and these two key reactions, the stereo-chemistry of the final products is well defined. In Step H of Scheme F, the amino terminus sidechain, designated $R^x$ is incorporated using coupling reaction A and $R^xCOOH$; the alkylation reaction C using $R^xCHO$ and a reducing agent; or alkylation reaction C using $R^xCH_2X^L$.

The alkane analogs are prepared in a similar manner by including an additional catalytic hydrogenation step as outlined in Reaction Scheme G.

REACTION SCHEME F

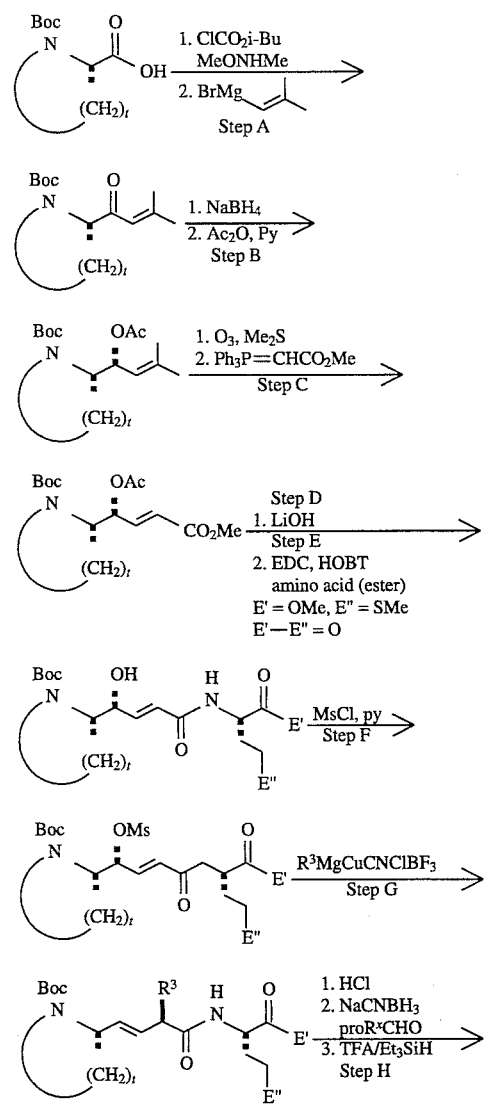

REACTION SCHEME F -continued
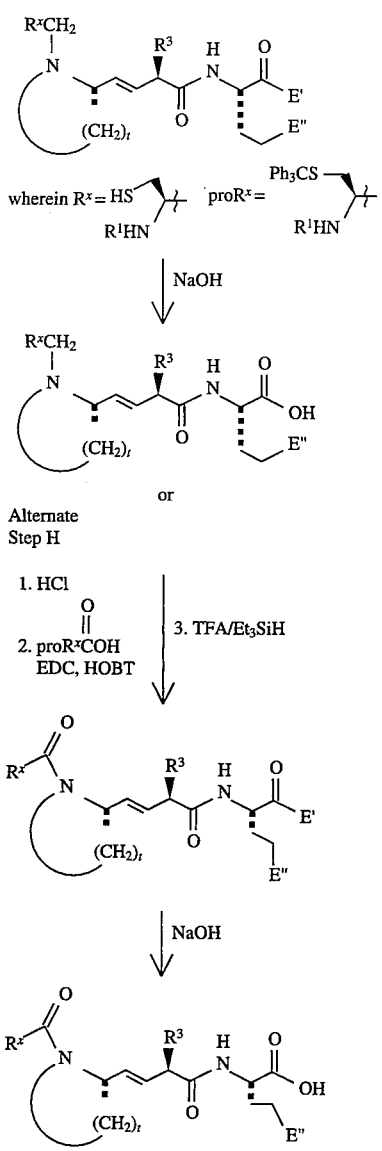
REACTION SCHEME G
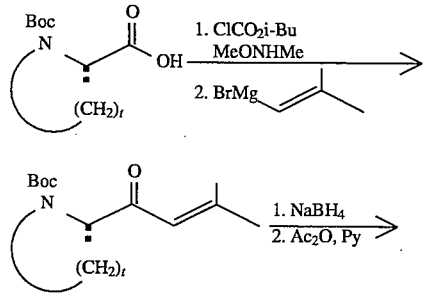
REACTION SCHEME G
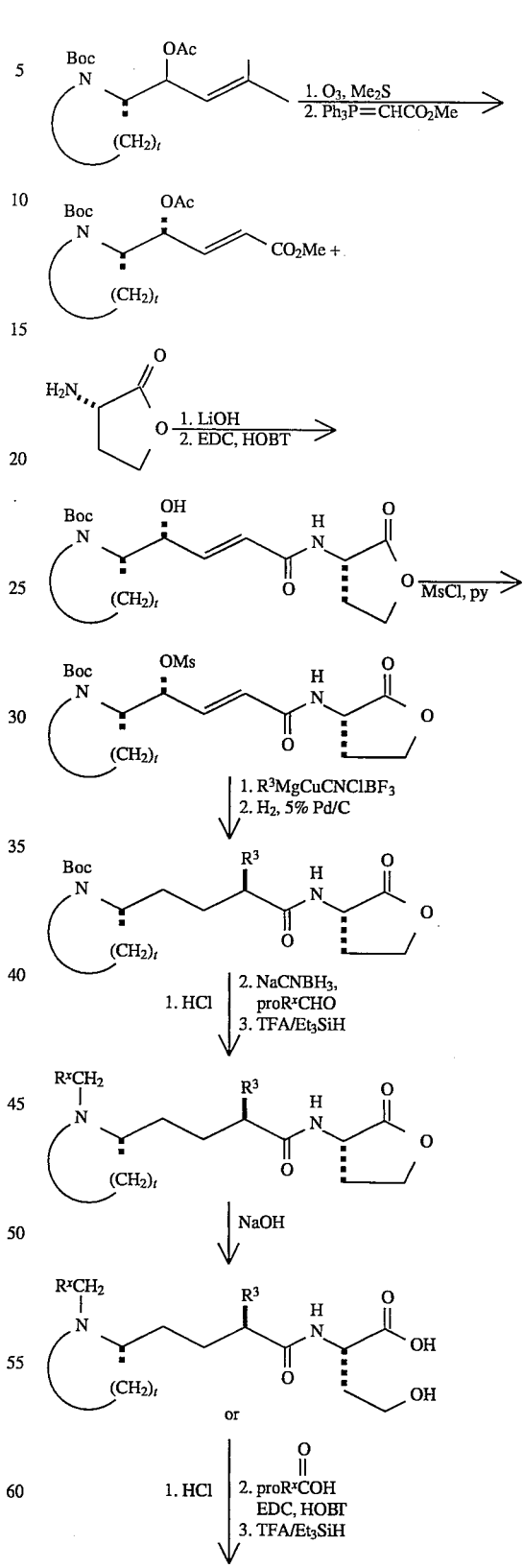

-continued
REACTION SCHEME G

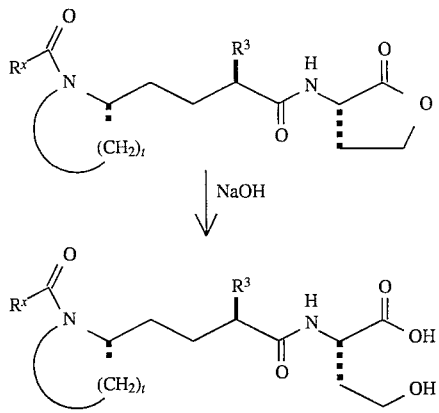

The oxa isostere compounds of this invention are prepared according to the route outlined in Scheme H. An aminoalcohol 1 is acylated with alpha-chloroacetyl chloride in the presence of trialkylamines to yield amide 2. Subsequent reaction of 2 with a deprotonation reagent (e.g., sodium hydride or potassium t-butoxide) in an ethereal solvent such as THF provides morpholinone 3. Alkylation of 3 with $R^3X^L$, where $X^L$ is a leaving group such as Br-, I- or Cl- in THF/DME (1,2-dimethoxyethane) in the presence of a suitable base, preferably NaHMDS [sodium bis(trimethylsilyl)amide], affords 4, which is retreated with NaHMDS followed by either protonation or the addition of an alkyl halide $R^4X$ to give 5a or 5a, respectively. Alternatively, 5a can be prepared from 3 via an aldol condensation approach. Namely, deprotonation of 3 with NaHMDS followed by the addition of a carbonyl compound $R^YR^ZCO$ gives the adduct 6. Dehydration of 6 can be effected by mesylation and subsequent elimination catalyzed by DBU (1,8diazabicyclo [5.4.0]undec-7-ene) or the direct treatment of 6 with phosphorus oxychloride in pyridine to give olefin 7. Then, catalytic hydrogenation of 7 yields 5a (wherein -$CHR^YR^Z$ constitutes $R^3$). Direct hydrolysis of 5 with lithium hydrogen peroxide in aqueous THF, or aqueous HCl, produces acid 8a. Compound 8a is then derivatized with BOC-ON or BOC anhydride to give 8b. The peptide coupling of acid 8b with either an alpha-aminolactone (e.g., homoserine lactone, etc.) or the ester of an amino acid is carried out under the conditions exemplified in the previously described references to yield derivative 9. Treatment of 9 with gaseous hydrogen chloride gives 10, which undergoes reductive alkylation in the presence of a protected aldehyde $proR^x$-CHO (11) and a reducing agent (e.g., sodium cyanoborohydride); or acylation in the presence of $proR^xCOOH$ (12) and a peptide coupling reagent affording, after removal of the trityl protecting group, the products 13 and 14. Hydrolysis of compounds 13 and 14 to the corresponding hydroxy acids and acids, respectively, is accomplished by standard methods such as treatment with NaOH in alcoholic or aqueous milieux followed by careful acidifcation with dilute HCl.

An alternative method for the preparation of the prolyl oxa isostere (compounds 23 and 24) is illustrated in Scheme H-1. Referring to Scheme H-1, the aminoalcohol 1 is protected with trifluoroacetic anhydride and the blocked compound 15 treated with diphenyl disulfide in the presence of tributylphosphine to provide the thioether 16. Chlorination of compound 16 provides compound 17 which can be reacted with the appropriate carboxylic acid alcohol in the presence of silver perchlorate and tin (II) chloride, to afford the mixed acetal 18. Removal of the phenylmercapto moiety with Raney nickel provides compound 19. Compound 19 is doubly deprotected, then selecteively BOC protected to provide acid 20, which undergoes the steps previously described for incorporating terminal amino acid. The appended free amine 22 then undergoes reductive alkylation in the presence of an aldehyde $proR^xCHO$ (11) and a reducing agent (e.g., sodium cyanoboro-hydride); or acylation in the presence of $proR^xCOOH$ (12) and a peptide coupling reagent affording, after removal of the trityl protecting group, the products 23 and 24. Hydrolysis of compounds 23 and 24 to the corresponding hydroxy acids and acids, respectively, is accomplished by standard methods such as treatment with NaOH in alcoholic or aqueous milieux followed by careful acidifcation with dilute HCl.

Yet another alternative method for the preparation of the prolyl oxa isostere (compounds 23 and 24 ) is described in the literature [Ruth E. TenBrink, *J. Org. Chem.*, 52:418–422 ( 1987)].

SCHEME H

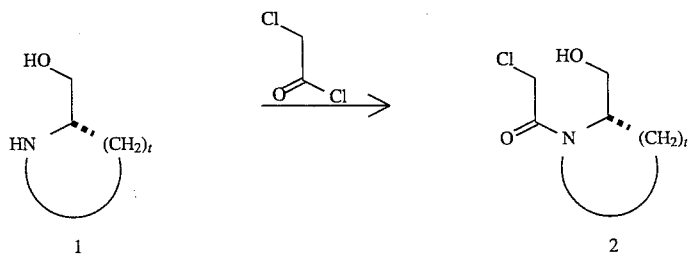

-continued
SCHEME H
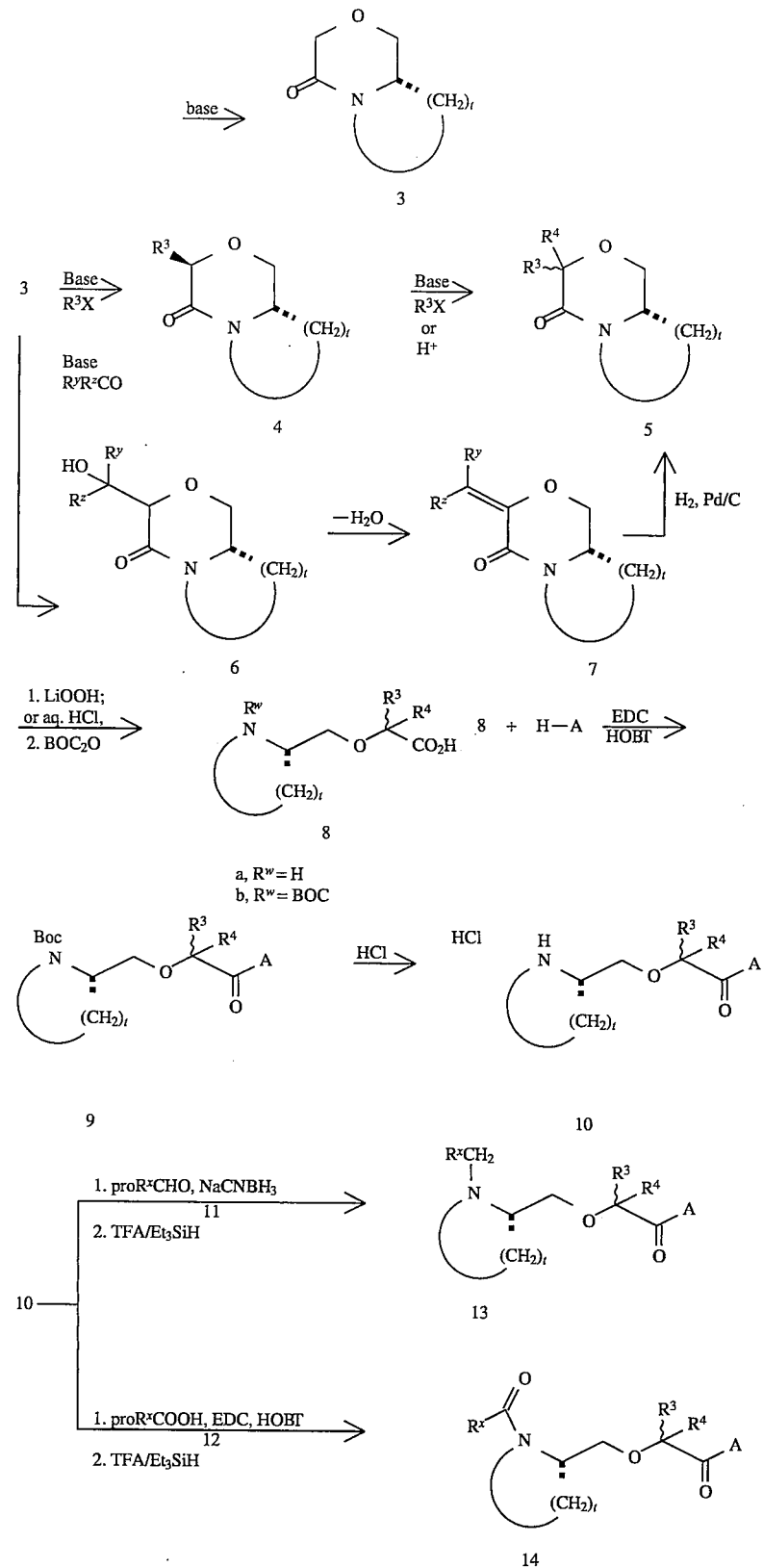

SCHEME H
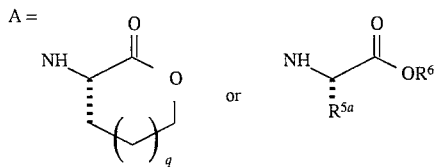
SCHEME H-1
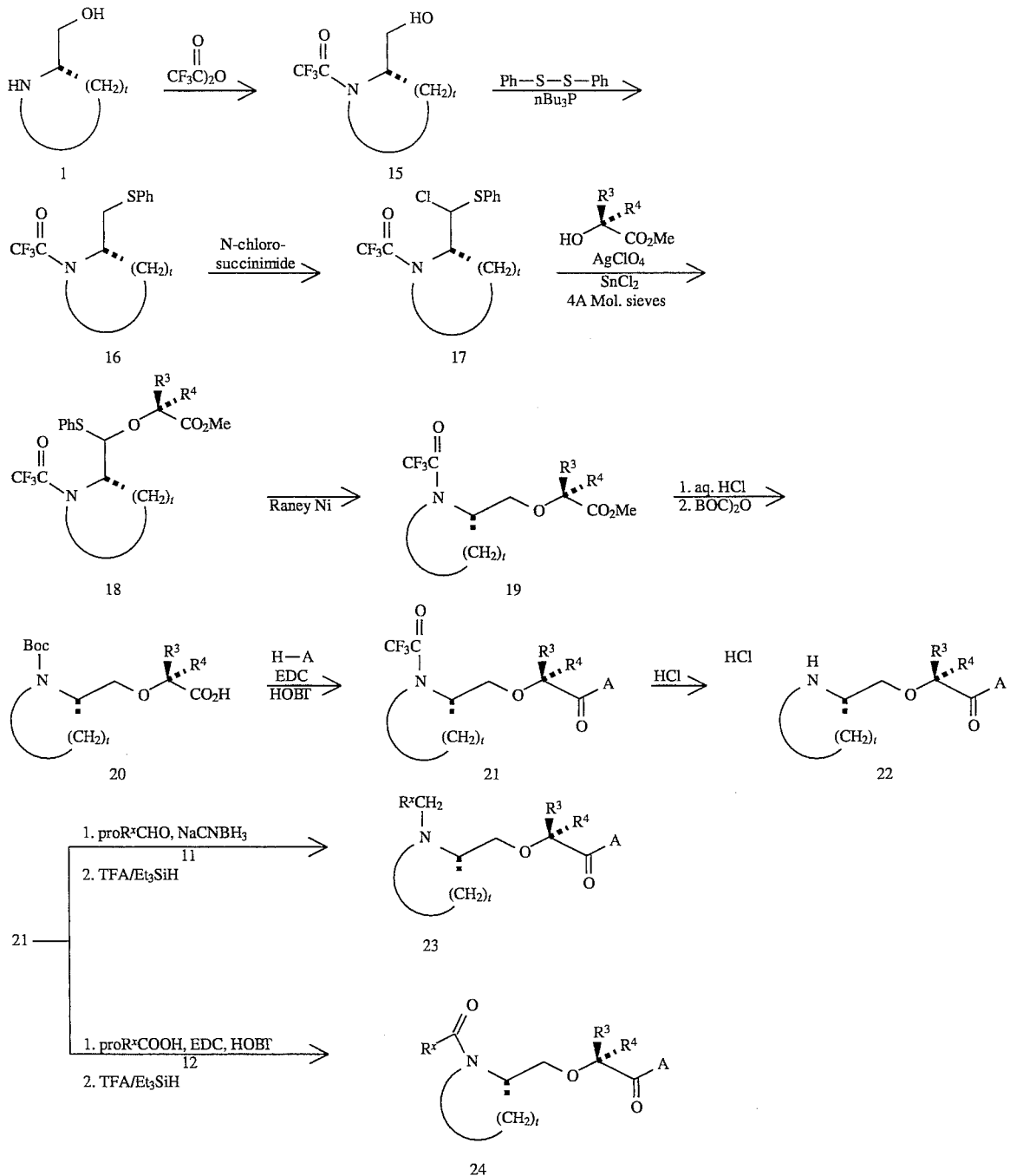

-continued
SCHEME H-1

A = 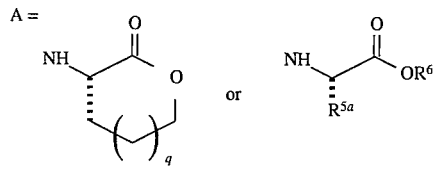

10

The thia, oxothia and dioxothia isostere compounds of this invention are prepared in accordance to the route depicted in Scheme I. Aminoalcohol 1 is derivatized with $BOC_2$ to give 25. Mesylation of 25 followed by reaction with methyl alpha-mercaptoacetate in the presence of cesium carbonate gives sulfide 26. Removal of the BOC group in 26 with TFA followed by neutralization with di-isopropylethylamine leads to 27. Sequential alkylation of 27 with the alkyl halides $R^3X$ and $R^4X$ in THF/DME using NaHDMS as the deprotonation reagent produces 28. Hydrolysis of 28 in hydrochloride to yield 29a, which is derivatized with Boc anhydride to yield 29b. The coupling of 29b with an alpha-aminolactone (e.g., homoserine lactone, etc.) or the ester of an amino acid is carried out under conventional conditions as exemplified in the previously described references to afford 30. Sulfide 30 is readily oxidized to sulfone 31 by the use of MCPBA (m-chloroperoxybenzoic acid). The N-BOC group of either 30 or 31 is readily removed by treatment with gaseous hydrogen chloride. The resultant amine hydrochloride 32 undergoes reductive alkylation in the presence of an aldehyde proR$^x$CHO (12) and a reducing agent (e.g., sodium cyanoborohydride); or acylation in the presence of proR$^x$COOH (13) and a peptide coupling reagent to afford, following removal of the trityl group, the products 33 and 34.

SCHEME I

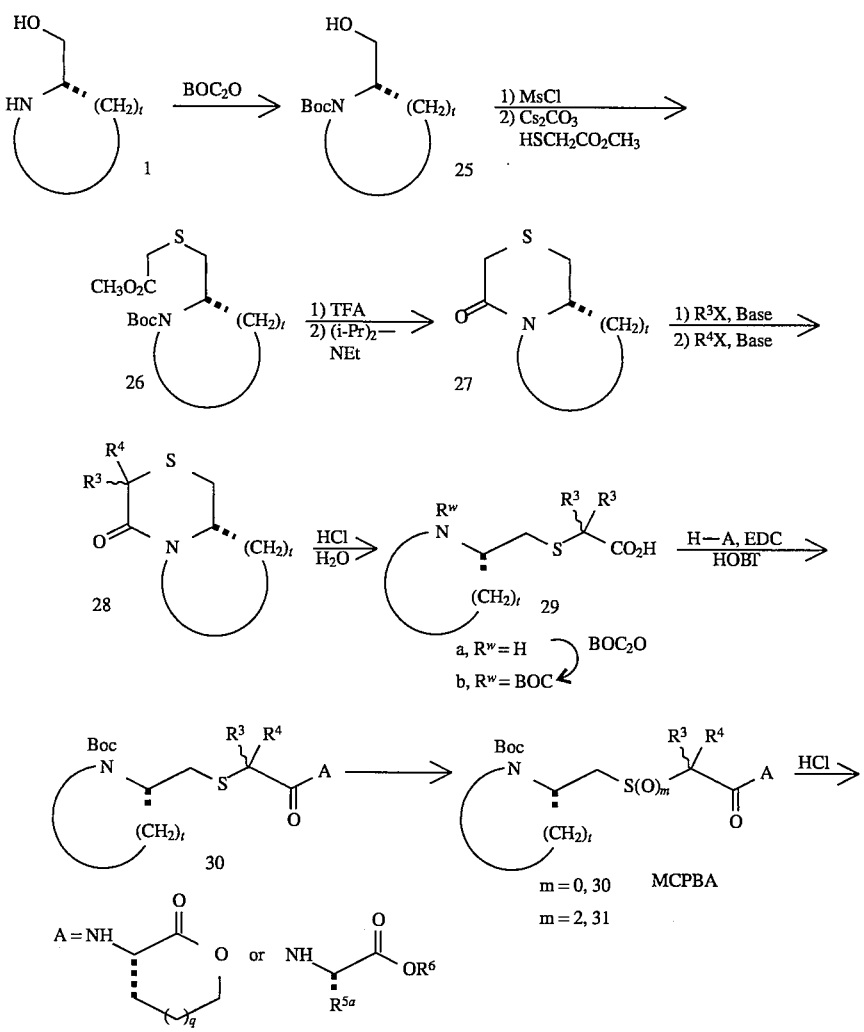

-continued
SCHEME I

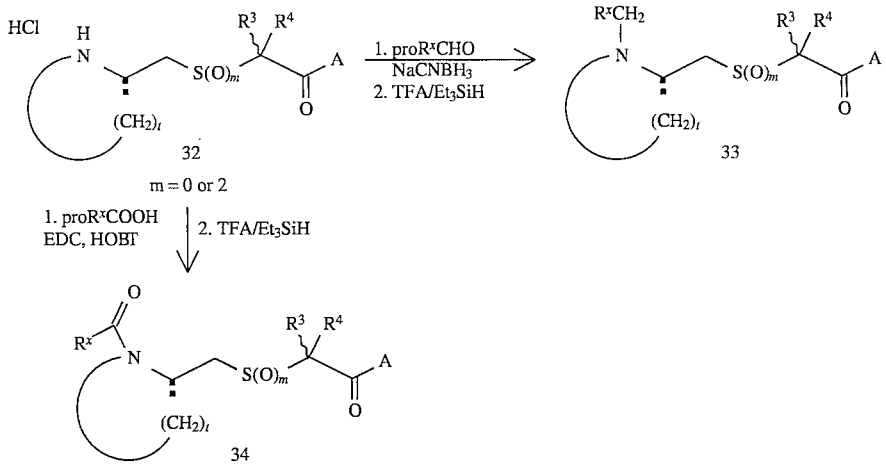

m = 0 or 2

The compounds of this invention inhibit Ras farnesyl transferase which catalyzes the first step in the post-translational processing of Ras and the biosynthesis of functional Ras protein. These compounds are useful as pharmaceutical agents for mammals, especially for humans. These compounds may be administered to patients for use in the treatment or cancer. Examples of the type of cancer which may be treated with tile compounds of this invention include, but are not limited to, colorectal carcinoma, exocrine pancreatic carcinoma, and myeloid leukemias.

The compounds of this invention may be administered to mammals, preferably humans, either alone or, prefrably, in combination with pharmaceutically acceptable carriers or diluents,. optionally with known adjuvants, such as alum, in a pharmaceutical composition, according to standard pharmaceutical practice. The compounds can be administered orally or parenterally, including intravenous, intramuscular, intraperitoneal, subcutaneous, rectal and topical routes of administration.

For oral use of a chemotherapeutic compound according to this invention, the selected compound may be administered, for example, in the form of tablets or capsules, or as an aqueous solution or suspension. In the case of tablets for oral use, carriers which are commonly used include lactose and corn starch, and lubricating agents, such as magnesium stearate, am commonly added. For oral administration in capsule form useful diluents include lactose and dried corn starch. When aqueous suspensions are required for oral use, the active ingredient is combined with emulsifying and suspending agents. If desired, certain sweetening and/or flavoring; agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's intramuscular blood-stream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 20 mg/kg of body weight per day, preferably of between 0.5 mg/kg of body weight to about 10 mg/kg of body weight per day.

The compounds of the instant invention are also useful as a component in an assay to rapidly determine the presence and quantity of farnesyl-protein transferase (FPTase) in a composition. Thus the composition to be tested may be divided and the two portions contacted with mixtures which comprise a known substrate of FPTase (for example a tetrapeptide having a cysteine at the amine terminus) and farnesyl pyrophosphate and, in one of the mixtures, a compound of the instant invention. After the assay mixtures are incubated for an sufficient period of time, well known in the art, to allow the FPTase to farnesylate the substrate, the chemical content of the assay mixtures may be determined by well known immunological, radiochemical or chromatographic techniques. Because the compounds of the instant invention are selective inhibitors of FPTase, absence or quantitative reduction of the amount of substrate in the assay mixture without the compound of the instant invention relative to the presence of the unchanged substrate in the assay containing the instant compound is indicative of the presence of FPTase in the composition to be tested.

It would be readily apparent to one of ordinary skill in the art that such an assay as described above would be useful in identifying tissue samples which contain farnesyl-protein transferase and quantitating the enzyme. Thus, potent inhibitor compounds of the instant invention may be used in an active site titration assay to determine the quantity of enzyme in the sample. A series of samples composed of aliquots of a tissue extract containing an unknown amount of farnesyl-protein transferase, an excess amount of a known substrate of FPTase (for example a tetrapeptide having a cysteine at the amine terminus) and farnesyl pyrophosphate are incubated for an appropriate period of time in the presence of varying concentrations of a compound of the instant invention. The concentration of a sufficiently potent inhibitor (i.e., one that has a Ki substantially smaller than the concentration of enzyme in the assay vessel) required to inhibit the enzymatic activity of the sample by 50% is approximately equal to half of the concentration of the enzyme in that particular sample.

EXAMPLES

Examples provided are intended to assist in a further understanding of the invention. Particular materials employed, species and conditions are intended to be further illustrative of the invention and not limitative of the reasonable scope thereof.

The standard workup referred to in the examples refers to solvent extraction and washing the organic solution with 10% citric acid, 10% sodium bicarbonate and brine as appropriate. Solutions were dried over sodium sulfate and evaporated in vacuo on a rotary evaporator.

EXAMPLE 1

Preparation of
N-[1-(2(R)-amino-3-mercaptopropyl)-2(S)-pyrrolidinylmethyl]-N-(1-naphthylmethyl)glycyl-methionine methyl ester tris trifluoroacetate salt Step A Preparation of N-[(2S)-(t-Butoxycarbonylpyrrolidinylmethyl)-glycine methyl ester N-(t-Butoxycarbonyl)-L-prolinal (9.16 g, 0.046 mol) and glycine methyl ester hydrochloride salt (5.78 g, 0.046 mol) were dissolved in MeOH (180 mL) at 0° C. under nitrogen, treated with sodium cyanoborohydride (4.34 g, 0.069 mol), and stirred for 18 h. The mixture was concentrated, and the residue was partitioned between EtOAc (100 mL) and satd aq NaHCO$_3$ soln (100 mL). The basic layer was washed with EtOAc (2×50 mL), the organics combined, washed with brine, and dried over Na$_2$SO$_4$). Filtration and concentration to dryness gave the title compound as a pale yellow oil. $^1$H NMR (CDCl$_3$) δ 3.7–3.9 (m, 1H), 3.72 (s, 3H), 3.43 (s, 2H), 3.33 (s, 2H), 2.7–2.9 (m, 1H), 2.5–2.65 (m, 1H), 1.75–2.0 (m, 4H), 1.47 (s, 9H).

Step B

Preparation of N-[(2S)-(t-Butoxycarbonylpyrrolidinylmethyl)-N-(1-naphthylmethyl) glycine methyl ester N-[(2S)-(t-Butoxycarbonylpyrrolidinylmethyl) glycine methyl ester (3.0 g, 0.011 mol) was dissolved in 1,2-dichloroethane (100 ml) and 3A molecular sieves (3 g) were added followed by 1-naphthaldehyde (1.63 ml, 0.012 mol) and sodium triacetoxyborohydride (4.64 g, 0.022 mol). The mixture was stirred at ambient temperature for 5 h, and filtered through glass fiber paper and concentrated. The residue was partitioned between EtOAc and sat. NaHCO$_3$ (100 ml/25 ml). The aqueous layer was washed with EtOAc (3×50 ml). The organic layers were combined, dried with Na$_2$SO$_4$, filtered, and concentrated to give crude product which was purified by chromatography (silica gel 1:6 EtOAc/hexane) to give the title compound. $^1$H NMR (CDCl) 67 8.24–8.4 (m, 1H), 7.7–7.9 (m, 2H), 7.35–7.5 (m, 4H), 4.43 (d, 1H, J=12 Hz), 3.8–4.1 (m, 2H). 3.68 (s, 3H), 3.15–3.5 (m, 4H), 2.94 (t, 1H, J=12 Hz)., 2.44 (t, 1H, J=11 Hz), 1.7–1.8 (m, 2H), 1.5–1.7 (m, 2H), 1.47 (s, 9H).

Step C

Preparation of N-[(2S)-(t-Butoxycarbonylpyrrolidinylmethyl)- N-(1-naphthymethyl)glycine N-[(2S)-(t-Butoxycarbonylpyrrolidinylmethyl)-N-(1-naphthylmethyl)glycine methyl ester (2.91 g, 7.10 mmol) was dissolved in MeOH (60 ml) and 1N NaOH (21.3 ml, 21.3 mmol) was added. The mixture was stirred at ambient temperature for 5 h and concentrated. The resulting residue was dissolved in H$_2$O (25 ml) and neutralized with 1N HCl (21.3 ml). The aqueous layer was washed with EtOAc (3×50 ml). The organic layers were combined, dried with Na$_2$SO$_4$, filtered, and concentrated to give product. $^1$H NMR (CD$_3$OD); δ 8.57 (d, 1H, J=9 Hz), 7.5–8.0 (m, 6H), 5.13 (d, 1H, J=12 Hz), 4.71 (d, 1H, J=12 Hz), 4.05–4.15 (m, 1H), 3.71 (ABq, 2H), 3.2–3.4 (m, 3H), 3.0–3.1 (m, 1H), 2.0–2.1 (m, 1H), 1.6–1.75 (m, 2H), 1.5–1.6 (m, 1H), 1.30 (s, 9H).

Step D

Preparation of N-[(2S)-(t-Butoxycarbonylpyrrolidinylmethyl)-N-(1-naphthylmethyl)glycine-methionine methyl ester N-[(2S)-(t-Butoxycarbonylpyrrolidinylmethyl)-N-(1-naphthylmethyl) glycine (1.44 g, 3.6 mmol), dissolved in CH$_2$Cl$_2$ (30 mL), was treated with HOBT (0.581 g, 4.3 mmol), EDC (0.831 g, 4.3 mmol), and methionine methyl ester hydrochloride (0.859 g, 4.3 mmol). The pH was adjusted to 7.5 with Et3N (1.1 mL, 7.9 mmol) and the mixture was stirred at ambient temperature for 18 h. The mixture was concentrated, and the residue was partitioned between CH$_2$Cl$_2$ (50 mL) and saturated NaHCO$_3$ solution (25 mL). The aqueous layer was extracted with CH$_2$Cl$_2$ (2×50 mL). The organic layers were combined, washed with brine (1×25 mL), dried (Na$_2$SO$_4$), filtered, and concentrated to give crude product which was purified by chromatography (silica gel eluting with 1:3 to 1:1 ethyl acetate in hexane) to give the title compound. $^1$H NMR (CDCl$_3$); δ 8.22 (d, 1H, J=9 Hz), 7.8–7.95 (m, 2H), 7.4–7.6 (m, 4H), 4.54 (d, 1H, J=16 Hz), 4.3–4.5 (m, 2H), 4.07–4.15 (m, 1H), 3.7–3.9 (m, 2H), 3.68 (s, 3H), 3.25–3.4 (m, 3H), 3.04–3.15 (m, 1H), 2.85–3.0 (m 1H), 2.4–2.5 (m, 1H), 1.89 (s, 3H). 1.53–2.5 (m, 5H), 1.48 (s. 9H), 1.2–1.45 (m, 2H).

Step E

Preparation of N-((2S)-pyrrolidinylmethyl)-N-(-1naphthyl-methyl)-glycyl-methionine methyl ester hydrochloride N-[(2S)-(t-Butoxycarbonylpyrrolidinylmethyl)-N-(1-naphthylmethyl)-glycyl-methionine methyl ester(1.5 g, 2.76 mmol) was dissolved in EtOAc (50 mL) and cooled to 0° C. HCl was bubbled through the mixture until TLC (95:5 CH$_2$Cl$_2$:MeOH) indicated complete reaction. Argon was bubbled through the mixture to remove excess HCl and the mixture was then concentrated to give the title compound. $^1$H NMR (CD$_3$OD); δ 8.23 (d, 1H, J=8 Hz), 7.9–7.95 (m, 2H), 7.45–7.65 (m, 4H), 4.4–4.6 (m, 4H). 3.7–3.8 (m,1H), 3.71 (s, 3H), 3.5–3.7 (m, 2H), 3.12–3.28 (m, 2H), 2.9–3.05 (m, 1H), 2.35–2.5 (m, 2H), 1.93–2.15 (m, 4H), 2.02 (s, 3H), 1.77–1.89 (m, 1H), 1.6–1.7 (m, 1H).

Anal. Calcd for C$_{24}$H$_{33}$N$_3$O$_3$S.2HCl .0.5H$_2$O:

C, 54.85; H, 6.90; N, 8.00

Found: C, 54.77; H, 6.72; N, 7.79

Step F

Preparation of N-[1-(2(R)-(t-butoxycarbonyl)amino-3triphenylmethylmercaptopropyl)-2(S)-pyrrolidinylmethyl ]- N-(1-naphthylmethyl)glycyl-methionine methyl ester N-((2S)-pyrrolidinylmethyl)-N-(1-naphthylmethyl)-glycylmethionine methyl ester hydrochloride (0.20 g, 0.39 mmol) was dissolved in MeOH (10 mL) in an ice-H$_2$O bath, treated with KOAc (0.15 g, 2.3 mmol), N-(t-butoxycarbonyl)-S-triphenylmethyl cysteinal (0.26 g, 0.59 mmol) and sodium cyanoborohydride (0.074 g, 1.17 mmol) then stirred at ambient temperature under argon for 18 h. The reaction mixture was filtered through glass fiber paper, concentrated, and partitioned between EtOAc and 5 % NH$_4$OH soln (50 mL/50 mL). The aqueous layer was washed with EtOAc (50 mL), organics combined, washed with brine (50 mL) and dried over Na$_2$SO$_4$. Filtration and concentration to dryness gave the title compound after chromatography on silica gel (CH$_2$Cl$_2$: MeOH, 98:2). $^1$H NMR (CD$_3$OD); δ 8.29 (d, 1H, J=9 Hz), 7.90 (d, 1H, J=9Hz), 7.81 (d, 1H, J=9 Hz), 7.3–7.55 (m, 19 H), 4.25–4.34 (m, 2H), 3.89 (d, 1H, J=16 Hz), 3.65 (s, 3H), 3.55–3.65 (m, 1H), 3.0–3.2 (m, 2H), 2.55–2.85 (m, 4H), 2.25–2.45 (m, 4H), 2.05–2.15 (m, 1H), 1.8–2.0 (m, 3H), 1.89 (s, 3H), 1.55–1.8 (m, 3H), 1.45 (s, 9H), 1.25–1.4 (m, 2H).

Step G

Preparation of N-[1-(2(R)-amino-3-mercaptopropyl)-2(S)-pyrrolidinylmethyl]-N-(1-naphthylmethyl)glycylmethionine methyl ester tris trifluoroacetate salt N-[1-(2(R)-(t-butoxycarbonyl)amino-3-triphenylmethyl mercaptopropyl)-2(S)-pyrrolidinylmethyl]- N-(1-naphthylmethyl)glycylmethionine methyl ester (0.129 g, 0.147 mmol) was dissolved in CH$_2$Cl$_2$ (2 mL) and treated with trifluoroacetic acid (TFA) (1 mL) and triethylsilane (0.094 mL, 0.589 mmol) with stirring at ambient temperature. After 4 h the mixture was concentrated, triturated with hexane, and the residue dissolved in 0.1% TFA/H$_2$O and chromatographed by RP HPLC to give the title compound. $^1$H NMR (CD$_3$OD); δ 8.20 (d, 1H, J=9 Hz), 7.85–7.95 (m, 2H), 7.5–7.65 (m, 4H), 4.62–4.68 (m, 1H), 4.40 (ABq, 2H), 3.7–3.8 (m, 1H), 3.73 (s, 3H), 3.35–3.6 (m, 4H), 3.0–3.3 (m, 6H), 2.8–2.9 (m, 1H), 2.65–2.8 (m, 1H), 2.4–2.6 (m, 2H), 2.06 (s, 3H), 1.85–2.2 (m, 4H), 1.62–0.7 (m, 1H). MS (M+1) 533.

EXAMPLE 2

Preparation of N-[1-(2(R)-amino-3-mercaptopropyl)-2(S)pyrrolidinylmethyl]-N-(1-naphthylmethyl)gycylmethionine Step A Preparation of N-[1-(2(R)-(t-butoxycarbonyl)amino-3-triphenylmethylmercaptopropyl)-2(S)-pyrrolidinylmethyl]-N-(1-naphthylmethyl)glycyl-methionine N-[1-(2(R)-(t-butoxycarbonyl)amino-3-triphenylmethylmercaptopropyl)-2(S)-pyrrolidinylmethyl]-N-(1-naphthylmethyl)glycylmethionine methyl ester from Example 1, Step F (0.091 g, 0.104 mmol) was dissolved in MeOH (2.5 mL) and 1N NaOH (0.416 mL, 0.416 mmol) with stirring at 0° C. After 6 h the mixture was concentrated, and the residue was partitioned between EtOAc and H$_2$O (25 mL/25 mL). The aqueous layer was washed with EtOAc (2×20 mL), the organics combined, washed with brine and dried over Na$_2$SO$_4$. Filtration and concentration gave the product. $^1$H NMR (CD$_3$OD); δ 8.05–8.1 (m, 1H), 7.75–7.90 (m, 2H), 7.15–7.5 (m, 19H), 4.35 (d, 1H, J=16 Hz), 4.05–4.25 (m, 2H), 3.6–3.7 (m, 1H), 3.44 (ABq, 2H), 2.93–3.05 (m, 1H), 2.75–2.95 (m, 2H), 2.6–2.75 (m, 2H) 2.25–2.6 (m, 5H), 2.04 (s 3H), 1.8–2.1 (m, 4H), 1.45–1.6 (m, 1H), 1.44 (s, 9H).

Step B

Preparation of N-[1-(2(R)-amino-3-mercaptopropyl)-2(S)-pyrrolidinylmethyl]-N-(1-naphthylmethyl)glycyl methionine tris trifluoroacetate salt N-[1-(2(R)-(t-butoxycarbonyl)amino-3-triphenylmethyl mercaptopropyl)-2(S )-pyrrolidinylmethyl]-N-(1-naphthylmethyl)glycylmethionine (0.089 g, 0.104 mmol) was deprotected as described in Example 1, Step G to give the title compound. $^1$H NMR (CD$_3$OD); δ 8.22 (d, 1 H, J=9 Hz), 7.94 (d, 1H, J=8 Hz), 7.89 (d, 1H, J=8 Hz), 7.5 –7.63 (m, 4H), 4.59–4.64 (m, 1H), 4.42 (ABq, 2H), 3.7–3.84 (m, 2H), 3.4–3.64 (m, 4H), 3.25–3.33 (m, 1H), 3.1–3.2 (m, 1H), .0–3.1 (m, 2H) 2.82–2.9 (m, 1H), 2.65–2.75 (m, 1H), 2.42–2.6 (m, 2H), 2.07 (s, 3H), 1.86–2.2 (m, 4H), 1.62–1.7 (m, 1H). MS (M+1) 519.

EXAMPLE 3

Preparation of 2(S)-[[1-[2(R or S)-Amino-3-mercapto]propyl]-2(S)-(pyrrolidinyl)methyloxyl]-3-phenylpropionylmethionine bis trifluoroacetate—diastereomer A Step A Preparation of N-Chloroacetyl-2(S)-hydroxymethypyrrolidine To a solution of 2(S)-hydroxymethylpyrrolidine (25.32 g, 0,250 mol) in CH$_2$Cl$_2$ (720 mL) under argon was added Et$_3$N (38.0 mL, 0,273 mol). After cooling this mixture to −20° C., chloroacetyl chloride (20.0 mL, 0.251 mol) was added dropwise over 0.75 h maintaining the reaction temperature at −20°±3° C. The reaction was stirred at ambient temperature for 18 h and evaporated in vacuo. An impurity which precipitated during concentration was removed by filtration. The crude product was purified by chromatography (silica gel, 1:39 to 1:19 MeOH/CH$_2$Cl$_2$) to give the title compound as a yellow oil. $^1$H NMR (CDCl$_3$, 400 MHz): δ 4.37 (dd, J=8,3 Hz, 1H), 4.22 (qd, J=7,3 Hz, 1H), 4.08 (s, 2H), 3.71 (td, J=8, 3 Hz, 1H), 3.68–3.50 (m, 3H), 2.14–1.86 (m, 3H), 1.72–1.62 (m, 1H).

Step B

Preparation of 6(S)-2-Oxo-1-aza-4-oxabicyclo-[4.3.0]-nonane

To a solution of N-chloroacetyl-2(S)-hydroxymethypyrrolidine (12.8 g, 0.072 mol) in THF (240 mL, distilled from Na/benzophenone) under argon at 0° C. was added NaH (3.16 g of a 60% dispersion in mineral oil. 0.079 mol) slowly in several portions. After complete addition, the reaction was stirred at ambient temperature for 18 h, then quenched by adding glacial acetic acid (400 mL), diluted with toluene, and evaporated in vacuo to give a thick gray liquid. Water was cautiously added dropwise until no further gas evolution was observed. This mixture was diluted with MeOH and CH$_2$Cl$_2$ and dried (Na$_2$SO$_4$). Since filtration was unsuccessful, silica gel (60 g) was added and the mixture was evaporated in vacuo. The crude product was purified by chromatography (silica gel, 7:13 to 1:1 EtOAc/CH$_2$Cl$_2$) to give the title compound as a white solid. $^1$H NMR (CDCl$_3$, 400 MHz): δ 4.25 (d, J=17 Hz, 1H), 4.19 (dd, J=12, 4 Hz, 1H), 4.02 (d, J=17 Hz, 1H), 3.76–3.64 (m, 2H), 3.50 (td, J=10, 2.5 Hz, 1H), 3.24 (dd, J=12, 10 Hz, 1H), 2.09–1.99 (m, 2H), 1.92–1.78 (m, 1H), 1.39 (qd, J=12, 8 Hz, 1H).

Step C

Preparation of 3(R),6(S)-2-Oxo-3-(phenylmethyl)-1-aza-4-oxabicyclo-[4.3.0]-nonane and 3(S),6(S)-2-Oxo-3-(phenylmethyl)-1-aza-4-oxabicyclo-[4.3.0]-nonane (93:7 respectively)

A solution of 6(S)-2-oxo-1-aza-4-oxabicyclo-[4.3.0]-nonane (6.013 g, 0.0426 mol) in THF (170 mL, distilled from Na/benzophenone) was cooled to −78° C. under argon and transferred via cannula to a second flask containing 1.0 M lithium bis(trimethylsilyl)amide in THF (52 mL, 0.052 mol) also at −78° C. under argon. After stirring for 0.5h at −78° C., benzyl bromide (7.20 mL, 0.0605 mol) was added dropwise over 5 min. The reaction was stirred for 1 h at −78° C. followed by 1 h at −50° C. then quenched by adding saturated aq NH$_4$Cl (60 mL) and warming to ambient temperature. The reaction was diluted with H$_2$O (60 mL) and saturated aq NaCl (180 mL), and the layers were separated. The aqueous layer was extracted twice with EtOAc (300, 200 mL). The organic extracts were washed in succession with saturated aq NaCl (150 mL), combined, dried (Na$_2$SO$_4$), and evaporated in vacuo. The crude product was purified by chromatography (silica gel, 1:4 EtOAc/CH$_2$Cl$_2$) to give the title compound as a yellow oil. $^1$H NMR (CDCl$_3$, 400 MHz): δ 7.31–7.19 (m, 5H), 4.44 (dd, J=10, 4 Hz, 0.07H), 4.27 (dd, J=8,4 Hz, 0.93H), 4.12 (dd, J=12, 4 Hz, 0.93H), 3.94 (dd, J=12, 5 Hz, 0.07H), 3.72–3.62 (m, 1H), 3.54–3.18 (m, 4H), 3.01 (dd, J=15, 8 Hz, 0.93H), 3.00 (dd, J=14, 8 Hz, 0.07H), 2.04–1.91 (m, 2H), 1.83–1.69 (m, 1H), 1.33 (qd, J=11, 8 Hz, 1H).

Step D

Preparation of 3(R),6(S)-2-Oxo-3-(phenylmethyl)-1-aza-4-oxabicyclo-[4.3.0]-nonane and 3(S),6(S)-2-Oxo-3-(phenylmethyl)-1-aza-4-oxabicyclo-[4.3.0]-nonane (2:1 respectively)

A soln of 3(R,S),6(S)-2-oxo-3-(phenylmethyl)-1-aza-4-oxabicyclo-[4.3.0]-nonane (8.818 g, 0.038 mol) in THF (170 mL, distilled from Na/benzophenone) was cooled to –78° C. under argor and transferred via cannula to a second flask containing 1.0 M lithium bis(trimethylsilyl)amide in tetrahydrofuran (57 mL, 0.057 mol) also at –78° C. under argon. After stirring for 10 min at –78° C., the reaction was placed in an ice bath for 0.5 h. The reaction was again cooled to –78° C. for 10 min, quenched by adding HOAc (3.30 mL), and allowed to warm to ambient temperature. The reaction was diluted with H$_2$O (50 mL) and saturated aq NaCl (100 mL) and extracted twice with EtOAc (300, 200 mL). The organic extracts were combined, washed with saturated aq NaCl (200 mL), dried (Na$_2$SO$_4$), and evaporated in vacuo to give the title compound as a golden orange oil. $^1$H NMR (CDCl$_3$, 400 MHz) δ 7.34–715 (m, 5H), 4.43 (dd, J=10, 3 Hz, 0.33H), 4.27 (dd, J=8, 3 Hz, 0.67H), 4.11 (dd, J=11,4 Hz, 0.67H), 3.94 (dd, J=11,4 Hz, 0.33H), 3.74–3.17 (m, 5H), 3.07 (dd, J=14, 10 Hz, 0.33H), 3.01 (dd, J=14, 8 Hz, 0.67H), 2.06–1.91 (m, 2H), 1.89–1.71 (m, 1H), 1.39–1.24 (m, 1H).

Step E

Preparation of 2(R)-[2(S)-(Pyrrolidinyl)methyloxy]-3-phenylpropionic acid hydrochloride and 2(S)-[2(S)-(Pyrrolidinyl)methyloxy]-3-phenylpropionic acid hydrochloride (2:1 respectively)

3(R,S),6(S)-2-Oxo-3-(phenylmethyl)-1-aza-4-oxabicyclo [4.3.0]-nonane (8.569 g, 0.037 mol) was dissolved in 6N aq HCl (400 mL) and stirred at reflux under argon for 24 h. The reaction was cooled to ambient temperature, evaporated in vacuo, diluted with toluene, evaporated in vacuo, diluted with toluene, and evaporated in vacuo to give the title compound as an orange oil. $^1$H NMR (CD3OD, 400 MHz) δ 7.35–7.10 (m, 5H), 4.33–4.26 (m, 1H), 3.84–3.53 (m, 3H), 3.30–3.09 (m, 3H), 3.05–2.96 (m, 1H), 2.17–1.88 (m, 3H), 1.80–1.65 (m, 1H).

Step F

Preparation of 2(R)-[1-(tert-Butoxycarbonyl)-2(S)-(pyrrolidinyl)methyloxy]-3-phenylpropionic acid and 2(S)-[N-(tert-Butoxycarbonyl)-2(S)-(pyrrolidinyl)methyloxy]-3-phenylpropionic acid (2:1 respectively)

2(R,S)-[2(S)-(Pyrrolidinyl)methyloxy]-3 -phenylpropionic acid hydrochloride (9.48 g, 0.033 mol) was dissolved in H$_2$O (70 ml) and neutralized with 1.0 N aq NaOH (approx. 40 mL). To this mixture was added a soln of Na$_2$CO$_3$ (7.304 g, 0.069 mol) in H$_2$O (40 mL). The resulting mixture (pH=11.5) was cooled to 0° C. under argon; di-tert-butyl dicarbonate (8.2 mL, 0.036 mol) was added, followed by THF. The reaction was stirred at ambient temperature for 18 h, cooled to 0° C., acidified to pH=3 with 10% aq citric acid, and extracted with EtOAc (2×250 mL). The organic extracts were washed in succession with saturated aq NaCl (250 mL), combined, dried (Na$_2$SO$_4$), and evaporated in vacuo to give the title compound as an orangish-brown oil. $^1$H NMR (CD$_3$OD, 400 MHz) δ 7.29–7.17 (m, 5H), 4.05–3.99 (m, 1H), 3.82–3.77 (m, 1H), 3.69–3.59 (m, 1H), 3.54–3.16 (m, 2H), 3.13–2.97 (m, 2H), 2.94–2.85 (m, 1H), 1.88–1.62 (m, 4H), 1.42 (s, 9H).

Step G

Preparation of 2(S)-[N-(tert-Butoxycarbonyl)-2(S)-(pyrrolidinyl)methyloxy]-3-phenylpropionyl-methionine methyl ester To a soln of 2(R,S)-[N-(tert-butoxycarbonyl)-2(S)-(pyrrolidinyl)methyloxy]-3-phenylpropionic acid (263.6 mg, 0.754 mmol) in DMF (8.0 mL) were added 3-hydroxy-1,2,3-benzotriazin-4(3H)-one (HOOBT, 137 mg, 0.840 mmol), EDC (164 mg, 0.855 mmol), L-methionine methyl ester hydrochloride (176 mg, 0.88 1 mmol), and Et$_3$N (0.35 mL, 2.5 mmol). The reaction was stirred under argon at ambient temperature for 18 h, diluted with EtOAc (70 mL), and washed with 10% aq citric acid (70 mL), saturated aq NaHCO$_3$ (40, 20 mL), and saturated aq NaCl (40 mL). The organic layer was dried (Na$_2$SO$_4$) and evaporated in vacuo. The diastereomeric crude products were purified and separated by chromatography (silica gel, 1:19 to 1:2 EtOAc/CH$_2$Cl$_2$) to give the title compound. $^1$H NMR (CD$_3$OD, 400 MHz) δ 7.35–7.17 (m, 5H), 4.63–4.55 (m, 1H), 4.08–3.90 (m, 2H), 3.72 (s, 3H), 3.55–3.46 (m, 2H), 3.34–3.22 (m, 1H), 3.09 (dd, J=14, 4 Hz, 1H), 2.91 (dd, J=14, 7 Hz, 1H), 2.38–2.20 (m, 2H), 2.10–2.00 (m, 1H), 2.04 (br s, 3H), 1.97–1.86 (m, 6H), 1.44 (s, 9H).

Step H

Preparation of 2(S)-[(2(S)-(Pyrrolidinyl)methyloxy]-3-phenylpropionyl-methionine methyl ester hydrochloride 2(S)-[N-(tert-Butoxycarbonyl)-2(S)-(pyrrolidinyl)-methyloxy]-3-phenylpropionyl-methionine methyl ester (2.138 g, 4.322 mmol) was dissolved in EtOAc (80 mL). The mixture was cooled to 0° C. and HCl gas was bubbled in until saturated. The mixture was stirred at ambient temperature for 1.25 h and evaporated in vacuo to give the title compound as a yellow foam which was used without further purification. $^1$H NMR (CD$_3$OD, 400 MHz) δ 7.35–7.20 (m, 5H), 4.67 (dd, J=10, 5 Hz, 1H), 4.21 (dd, J=8, 5 Hz, 1H), 3.81–3.75 (m, 2H), 3.75 (s, 3H), 3.58 (q, J=6 Hz, 1H), 3.30–3.11 (m, 3H), 2.99 (dd, J=14, 8 Hz, 1H), 2.53–2.36 (m, 2H), 2.19–2.10 (m, 1H), 2.08 (s, 3H), 2.07–1.88 (m, 4H), 1.79–1.68 (m, 1H).

Step I Preparation of 2(S )-[[N-[2(R,S)-(tert-Butoxycarbonyl)-amino-3-triphenyhnethylmercapto]propyl]-2(S)-(pyrro-lidinyl)methyloxy]-3-phenylpropionyl-methionine methyl ester—diastereomers A and B 2(S)-[(2(S)-(Pyrrolidinyl)methyloxy]-3-phenylpropionyl-methionine methyl ester hydrochloride (69.0 mg, 0.160 mmol) was dissolved in MeOH (1.40 mL). N-(t-Butoxycarbonyl)-S-triphenyl methylcysteine aldehyde (95.6 mg, 0.214 mmol) was added followed by 4A molecular sieves (0.26 g), KOAc (17.4 mg, 0.183 mmol) and 1.0 M sodium cyanoborohydride in THF (0.21 mL, 0.21 mmol). The mixture was stirred under argon at ambient temperature for 18 h and filtered. The filtrate was diluted with EtOAc (15 mL), and washed with saturated aq NaHCO$_3$ (15 mL) and saturated aq NaCl (15 mL). The organic layer was dried (Na$_2$SO$_4$) and evaporated in vacuo to give crude material which was purified by chromatography (silica gel, 1:4 EtOAc/CH$_2$Cl$_2$) to give the high R$_f$ diastereomer (A) and the low R$_f$ diastereomer (B) of the title compound.

High $R_f$ diastereomer (A): $^1$H NMR (CD$_3$OD, 400 MHz) δ 7.41–7.35 (m, 6H), 7.30–7.16 (m, 14H), 4.59 (dd, J=9, 5 Hz, 1H) 3.96 (dd, J=8, 4 Hz, 1H), 3.75–3.54 (m, 1H), 3.68 (s, 3H), 3.42–3.20 (m, 3H), 3.05 (dd, J=13, 5 Hz, 1H), 2.89 (dd, J=14, 7 Hz, 1H), 2.88–2.78 (m, 1H), 2.68–2.54 (m, 2H), 2.40–2.14 (m, 5H), 2.10–1.96 (m, 1H), 2.03 (s, 3H), 1.94–1.82 (m, 1H), 1.82–1.70 (m, 1H), 1.69–1.54 (m, 2H), 1.54–1.42 (m, 1H), 1.45 (s, 9H).

Low $R_f$ diastereomer (B): $^1$H NMR (CD$_3$OD, 400 MHz) δ 7.43–7.36 (m, 6H), 7.33–7.15 (m, 14H), 4.59 (dd, J=9, 5 Hz, 1H), 3.99 (dd, J=8, 4 Hz, 1H), 3.74–3.60 (m, 2H), 3.65 (s, 3H), 3.47 (dd, J=10, 5 Hz, 1H), 3.14–2.70 (m, 7H), 2.65–2.52 (m, 2H), 2.42–2.23 (m, 3H), 2.23–2.11 (m 1H), 2.03 (s, 3H), 1.98–1.85 (m, 1H), 1.82–1.55 (m, 3H), 1.45 (s, 9H).

Step J

Preparation of 2(S)-[[N-[2(R,S)-(tert-Butoxy-carbonyl)-amino-3-triphenylmethylmercapto]propyl]-2(S)-(pyrrolidinyl)methyloxy]-3-phenylpropionyl-methionine—diastereomer A 2(S)-[[N-[2(R,S)-(tert-Butoxycarbonyl)-amino-3-triphenylmethylmercapto]propyl]2(S)-(pyrrolidinyl)methyloxy]-3-phenylpropionyl-methionine methyl ester—diastereomer A (27.6 mg, 0.0334 mmol) was dissolved in MeOH (0.8 mL) under argon. 1.0 N aq LiOH (37 mL, 0.037 mmol) was added and the mixture was stirred at ambient temperature for 18 h. Additional 1.0 N aq LiOH (18 mL, 0.018 mmol) was added. After stirring for 3 h at ambient temperature, the reaction was evaporated in vacuo, diluted with MeOH (1 mL), neutralized with glacial acetic acid (1 drop), and evaporated in vacuo to give the title compound (crude) which was used without further purification or characterization.

Step K

Preparation of 2(S)-[[N-[2(R,S)-amino-3-mercapto]propyl]-2(S)-(pyrrolidinyl)methyloxy]-3-phenylpropionyl-methionine bis trifluoroacetate—diastereomer A 2(S)-[[N-[2(R,S)-(tert-Butoxycarbonyl)-amino-3triphenylmethylmercapto]-propyl]-2(S)-(pyrrolidinyl)methyloxy]-3-phenylpropionyl-methionine—diastereomer A (34.7 mg crude, 0.0334 mmol), dissolved in CH$_2$Cl$_2$ (1 mL) under argon was treated with TFA (0.5 mL) followed by triethylsilane (50 mL). The mixture was stirred at ambient temperature for 5 h. The mixture was evaporated in vacuo and the residue purified by preparative HPLC using a NovaPrep 5000 Semi Preparative HPLC System and a Waters PrepPak cartridge (47×300 mm, C18, 15 mm, 100 A) eluting with 5–95% acetonitrile/water (0.1% TFA) at 100 mL/min to give the title compound. $^1$H NMR (CD$_3$OD, 400 MHz) δ 7.32–7.20 (m, 5H), 4.61 (dd, J=10,5 Hz, 1H), 4.25 (dd, J=8, 5 Hz, 1H),3.83–3.74 (m, 1H),3.71 (dd, J=12, 4 Hz, 1H), 3.64 (dd, J=12, 5 Hz, 1H), 3.59–3.45 (m, 3H), 3.27–3.12 (m, 2H), 3.09–2.85 (m, 4H), 2.59–2.39 (m, 2H), 2.23–1.90 (m, 5H), 2.09 (s, 3H), 1.87–1.75 (m, 1H). FAB HRMS exact mass calc'd for C$_{22}$H$_{36}$N$_3$O$_4$S$_2$.470.214726 (MH$^+$); found 470.213392.

Anal. Calc'd for C$_{22}$H$_{35}$N$_3$O$_4$S$_2$.2.40 CF$_3$CO$_2$H.0.45 H$_2$O: C, 42.84: H, 5.14; N, 5.59
Found: C, 42.82; H, 5.11; N, 5.79

EXAMPLE 4

Preparation of
2(S)-[[N-[2(R,S)-amino-3-mercapto]propyl]-2(S)-(pyrrolidinyl)methyloxy]-3-phenylpropionyl-methionine bis trifluoroacetate—diastereomer B The title compound was prepared according to the methods of Example 3, Steps J and K, using the low $R_f$ diastereomer (B) instead of the high $R_f$ diastereomer (A) obtained from Step I. $^1$H NMR (CD$_3$OD, 400 MHz) δ 7.34–7.21 (m, 5H), 4.60 (dd, J=10, 5 Hz, 1H), 4.22 (dd, J=10, 5 Hz, 1H), 3.78–3.66 (m, 2H), 3.64–3.56 (m, 2H), 3.50–3.38 (m, 2H), 3.14 (dd, J=14, 5 Hz, 1H), 3.09–2.80 (m, 2H), 2.87 (br d, J =6 Hz, 2H), 2.58–2.39 (m, 2H), 2.22–1.80 (m, 7H), 2.09 (s, 3H). FAB HRMS exact mass calc'd for C$_{22}$H$_{36}$N$_3$O$_4$S$_2$: 470.214726 (MH$^+$); found 470.214101.

EXAMPLE 5

In vitro inhibition of ras farnesyl transferase

Assays of Farnesyl-Protein Transferase.

Partially purified bovine FPTase and Ras peptides (Ras-CVLS, Ras-CVIM and RAS-CAIL) were prepared as described by Schaber et al., *J. Biol. Chem.* 265:14701–14704 (1990), Pompliano, et al., *Biochemistry* 31:3800 (1992) and Gibbs et al., *PNAS U.S.A.* 86:6630–6634 (1989). Bovine FPTase was assayed in a volume of 100 μl containing 100 mM N-(2hydroxy ethyl) piperazine-N'-(2-ethane sulfonic acid) (HEPES), pH 7.4, 5 mM MgCl$_2$, 5 mM dithiothreitol (DTT), 100 mM [$^3$H]-farnesyl diphosphate ([$^3$H]-FPP; 740 CBq/mmol, New England Nuclear), 650 nM Ras-CVLS and 10 μg/ml FPTase at 31° C. for 60 min. Reactions were initiated with FPTase and stopped with 1 ml of 1.0 M HCL in ethanol. Precipitates were collected onto filter-mats using a TomTec Mach II cell harvestor, washed with 100% ethanol, dried and counted in an LKB β-plate counter. The assay was linear with respect to both substrates, FPTase levels and time; less than 10% of the [$^3$H]-FPP was utilized during the reaction period. Purified compounds were dissolved in 100% dimethyl sulfoxide (DMSO) and were diluted 20-fold into the assay. Percentage inhibition is measured by the amount of incorporation of radioactivity in the presence of the test compound when compared to the amount of incorporation in the absence of the test compound.

Human FPTase was prepared as described by Omer et al., *Biochemistry* 32:5167–5176 (1993). Human FPTase activity was assayed as described above with the exception that 0.1% (w/v) polyethylene glycol 20,000, 10 μM ZnCl$_2$ and 100 nM Ras-CVIM were added to the reaction mixture. Reactions were performed for 30 min., stopped with 100 μl of 30% (v/v) trichloroacetic acid (TCA) in ethanol and processed as described above for the bovine enzyme.

The compounds of the instant invention were tested for inhibitory activity against human FPTase by the assay described above and were found to have IC$_{50}$ of <10 μM.

EXAMPLE 6

In vivo ras farnesylation assay

The cell line used in this assay is a v-ras line derived from either Rat1 or NIH3T3 cells, which expressed viral Ha-ras p21. The assay is performed essentially as described in DeClue, J.E. et al., *Cancer Research* 51:712–717, (1991). Cells in 10 cm dishes at 50–75% confluency are treated with the test compound (final concentration of solvent, methanol or dimethyl sulfoxide, is 0.1%). After 4 hours at 37° C., the cells are labelled in 3 ml methionine-free DMEM supplemeted with 10% regular DMEM, 2% fetal bovine serum and 400 mCi[$^{35}$S]methionine (1000 Ci/mmol). After an additional 20 hours, the cells are lysed in 1 ml lysis buffer (1% NP40/20 mM HEPES, pH ;7.5/5 mM MgCl$_2$/1 mM DTT/10 mg/ml aprotinen/2 mg/ml leupeptin/2 mg/ml antipain/0.5 mM PMSF) and the lysates cleared by centrifugation at 100,000×g for 45 min. Aliquots of lysates containing equal numbers of acid-precipitable counts are bought to 1 ml with IP buffer (lysis buffer lacking DTT) and immunoprecipitated with the ras-specific monoclonal antibody Y13–259 (Furth, M.E. et al., *J. Virol.* 43:294–304, (1982)). Following a 2 hour antibody incubation at 4° C., 200 ml of a 25% suspension of protein A-Sepharose coated with rabbit anti rat IgG is added for 45 min. The immunoprecipitates are washed four times with IP buffer (20 nM HEPES, pH 7.5/1 mM EDTA/1% Triton X-100.0.5% deoxycholate/0.1%/SDS/0.1 M NaCl) boiled in SDS-PAGE sample buffer and loaded on 13% acrylamide gels. When the dye front reached the bottom, the gel is fixed, soaked in Enlightening, dried and autoradiographed. The intensities of the bands corresponding to farnesylated and nonfarnesylated ras proteins am compared to determine the percent inhibition of farnesyl transfer to protein.

EXAMPLE 7

In vivo growth inhibition assay

To determine the biological consequences of FPTase inhibition, the effect of the compounds of the instant invention on the anchorage-independent growth of Rat 1 cells transformed with either a v-ras, v-raf, or v-mos oncogene is tested. Cells transformed by v-Raf and v-Mos maybe included in the analysis to evaluate the specificity of instant compounds for Ras-induced cell transformation.

Rat 1 cells transformed with either v-ras, v-raf, or v-mos are seeded at a density of $1\times10^4$ cells per plate (35 mm in diameter) in a 0.3% top agarose layer in medium A (Dulbecco's modified Eagle's medium supplemented with 10% fetal bovine serum) over a bottom agarose layer (0.6%). Both layers contain 0.1% methanol or an appropriate concentration of the instant compound (dissolved in methanol at 1000 times the final concentration used in the assay). The cells are fed twice weekly with 0.5 ml of medium A containing 0.1% methanol or the concentration of the instant compound. Photomicrographs are taken 16 days after the cultures are seeded and comparisons are made.

What is claimed is:

1. A compound which inhibits Ras farnesyltransferase having the formula I:

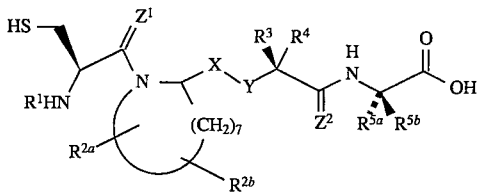

I wherein:
$R^1$ is selected from:
  a) hydrogen,
  b) $R^8S(O)_2$-, $R^8C(O)$-, $(R^8)_2NC(O)$- or $R^9OC(O)$-, and
  c) $C_1$–$C_6$ alkyl unsubstituted or substituted by aryl, cycloalkyl, alkenyl, alkynyl, $R^8O$-, $R^8S(O)_m$-, $R^8C(O)NR^8$-, CN, $(R^8)_2N$-C(NR^8)-, $R^8C(O)$-, $R^8OC(O)$-, $N_3$, —$N(R^8)_2$, or $R^9OC(O)NR^8$-;

$R^{2a}$ is selected from:
  a) hydrogen,
  b) substituted or unsubstituted $C_1$–$C^{10}$ alkyl, $C_2$–$C_{10}$ alkenyl, $C_3$–$C_{10}$ cycloalkyl or aryl group,
    wherein the substituent is selected from F, Cl, B, $NO_2$, $R^8O$-, $R^8S(O)_m$, $R^8C(O)NR^8$-, CN, $(R^8)_2N$-C(NR^8)-, $R^8C(O)$-, $R^8OC(O)$-, $N_3$, —$N(R^8)_2$, $R^9OC(O)NR^8$- and $C_1$–$C_{20}$ alkyl,
  c) $R^8O$-, $R^8S(O)_m$-, $R^8C(O)NR^8$-, CN, $NO_2$, $(R^8)_2N$-C(NR^8)-, $R^8C(O)$-, $R^8OC(O)$-, $N_3$, —$N(R^8)_2$, or $R^9OC(O)NR^8$-,
  d) $C_1$–$C_6$ alkyl substituted with an unsubstituted or substituted group selected from aryl and $C_3$–$C_{10}$ cycloalkyl, and
  e) a side chain of a naturally occurring amino acid, wherein the amino acid is selected from alanine, leucine, isoleucine, norleucine, valine and norvaline;

$R^{2b}$ is selected from:
  a) hydrogen,
  b) $C_1$–$C_6$ alkyl unsubstituted or substituted by alkenyl, $R^8O$-, $R^8S(O)_m$-, $R^8C(O)NR^8$-, CN, $(R^8)_2N$-C(NR^8)-, $R^8C(O)$-, $R^8OC(O)$-, $N_3$, —$N(R^8)_2$, or $R^9OC(O)NR^8$-,
  c) aryl, cycloalkyl, alkenyl, $R^8O$-, $R^8S(O)_m$-, $R^8C(O)NR^8$-, CN, $NO_2$, $(R^8)_2N$-C(NR^8)-, $R^8C(O)$-, $R^8OC(O)$-, $N_3$, —$N(R^8)_2$, or $R^9OC(O)NR^8$-, and
  d) $C_1$–$C_6$ alkyl substituted with an unsubstituted or substituted group selected from aryl and $C_3$–$C_{10}$ cycloalkyl;

$R^3$ and $R^4$ are independently selected from:
  a) a side chain of a naturally occurring amino acid,
  b) an oxidized form of a side chain of a naturally occurring amino acid which is:
    i) methionine sulfoxide, or
    ii) methionine sulfone,
  c) substituted or unsubstituted $C_1$–$C_{20}$ alkyl, $C_2$–$C_{20}$ alkenyl, $C_3$–$C_{10}$ cycloalkyl or aryl group,
    wherein the substituent is selected from F, Cl, Br, $N(R^8)_2$, $NO_2$, $R^8O$-, $R^8S(O)_m$, $R^8C(O)NR^8$-, CN, $(R^8)_2N$- C(NR^8)-, $R^8C(O)$-, $R^8OC(O)$-, $N_3$, —$N(R^8)_2$, $R^9OC(O)NR^8$- and $C_1$–$C_{20}$ alkyl, and
  d) $C_1$–$C_6$ alkyl substituted with an unsubstituted or substituted group selected from aryl and $C_3$–$C_{10}$ cycloalkyl; or $R^3$ and $R^4$ are combined to form —$(CH_2)_s$-;

$R^{5a}$ and $R^{5b}$ are independently selected from:
  a) a side chain of a naturally occurring amino acid,
  b) an oxidized form of a side chain of a naturally occurring amino acid which is:
    i) methionine sulfoxide, or
    ii) methionine sulfone,
  c) substituted or unsubstituted $C_1$–$C_{20}$ alkyl, $C_2$–$C_{20}$ alkenyl, $C_3$–$C_{10}$ cycloalkyl or aryl group,
    wherein the substituent is selected from F, Cl, Br, $N(R^8)_2$, $NO_2$, $R^8O$-, $R^8S(O)_m$-, $R^8C(O)NR^8$-, CN, $(R^8)_2N$-C(NR^8)-, $R^8C(O)$-, $R^8OC(O)$-, $N_3$, —$N(R^8)_2$, $R^9OC(O)NR^8$- and $C_1$–$C_{20}$ alkyl, and
  d) $C_1$–$C_6$ alkyl substituted with an unsubstituted or substituted group selected from aryl and $C_3$–$C_{10}$ cycloalkyl; or $R^{5a}$ and $R^{5b}$ are combined to form —$(CH_2)_s$—;

X-Y is

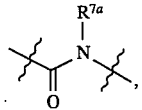 a)

49

-continued

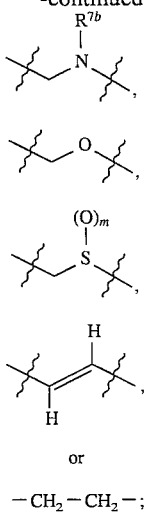

b)

R⁷ᵃ is selected from
 a) hydrogen,
 b) unsubstituted or substituted aryl,
 c) unsubstituted or substituted cycloalkyl, and
 d) $C_1-C_6$ alkyl substituted with hydrogen or an unsubstituted or substituted group selected from aryl and cycloalkyl;

R⁷ᵇ is selected from
 a) hydrogen,
 b) unsubstituted or substituted aryl,
 c) unsubstituted or substituted cycloalkyl,
 d) $C_1-C_6$ alkyl substituted with hydrogen or an unsubstituted or substituted group selected from aryl and cycloalkyl,
 e) a carbonyl group which is bonded to an unsubstituted or substituted group selected from aryl, cycloalkyl and $C_1-C_6$ alkyl substituted with hydrogen or an unsubstituted or substituted group selected from aryl and cycloalkyl, and,
 f) a sulfonyl group which is bonded to an unsubstituted or substituted group selected from aryl, cycloalkyl and $C_1-C_6$ alkyl substituted with hydrogen or an unsubstituted or substituted group selected from aryl and cycloalkyl;

$R^8$ is independently selected from hydrogen, $C_1-C_6$ alkyl and aryl;

$R^9$ is independently selected from $C_1-C_6$ alkyl and aryl;

$Z^1$ and $Z^2$ are independently $H_2$ or O, provided that $Z^1$ is not O when

X-Y is —C(O)N(R⁷a)—;

m is 0, 1 or 2;
s is 4 or 5; and
t is 3;

or a pharmaceutically acceptable salt thereof.

50

2. A compound according to claim 1 which has the formula I:

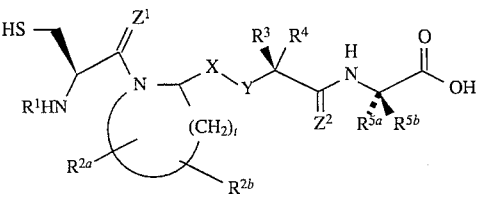

wherein:
$R^1$ is selected from:
 a) hydrogen,
 b) $R^8S(O)_2-$, $R^8C(O)-$, $(R^8)_2NC(O)-$ or $R^9OC(O)-$, and
 c) $C_1-C_6$ alkyl unsubstituted or substituted by aryl, cycloalkyl, alkenyl, alkynyl, $R^8O-$, $R^8S(O)_m-$, $R^8C(O)NR^8-$, CN, $(R^8)_2N-C(NR^8)-$, $R^8C(O)-$, $R^8OC(O)-$, $N_3$, $—N(R^8)_2$, or $R^9OC(O)NR^8-$;

$R^{2a}$ is selected from:
 a) a side chain of a naturally occurring amino acid, wherein the amino acid is selected from alanine, leucine, isoleucine, norleucine, valine and norvaline;
 b) substituted or unsubstituted $C_1-C_{10}$ alkyl, $C_2-C_{10}$ alkenyl, $C_{3C10}$ cycloalkyl or aryl group,
  wherein the substituent is selected from F, Cl, Br, $NO_2$, $R^8O-$, $R^8S(O)_m-$, $R^8C(O)NR^8-$, CN, $(R^8)_2N-C(NR^8)-$, $R^8C(O)-$, $R^8OC(O)-$, $N_3$, $—N(R^8)_2$, $R^9OC(O)NR^8-$ and $C_1-C_{20}$ alkyl, and
 c) $C_1-C_6$ alkyl substituted with an unsubstituted or substituted group selected from aryl and $C_3-C_{10}$ cycloalkyl; and $R^{2b}$ is selected from hydrogen and $C_1-C_6$ alkyl;
$R^3$ and $R^4$ are independently selected from:
 a) a side chain of a naturally occurring amino acid,
 b) an oxidized form of a side chain of a naturally occurring amino acid which is:
  i) methionine sulfoxide, or
  ii) methionine sulfone,
 c) substituted or unsubstituted $C_1-C_{10}$ alkyl, $C_2-C_{10}$ alkenyl, $C_3-C_{10}$ cycloalkyl or aryl group,
  wherein the substituent is selected from F, Cl, Br, $NO_2$, $R^8O-$, $R^8S(O)_m-$, $R^8C(O)NR^8-$. CN, $(R^8)_2N-C(NR^8)-$, $R^8C(O)-$, $R^8OC(O)-$. $N_3$, $—N(R^8)_2$, $R^9OC(O)NR^8-$ and $C_1-C_{20}$ alkyl, and
 d) $C_1-C_6$ alkyl substituted with an unsubstituted or substituted group selected from aryl and $C_3-C_{10}$ cycloalkyl;

$R^{5a}$ is selected from:
 a) a side chain of a naturally occurring amino acid, wherein the amino acid is selected from methionine and glutamine,
 b) an oxidized form of a side chain of a naturally occurring amino acid which is:
  i) methionine sulfoxide, or
  ii) methionine sulfone,
 c) substituted or unsubstituted $C_1-C_{10}$ alkyl, $C_2-C_{10}$ alkenyl, $C_3-C_{10}$ cycloalkyl or aryl group,
  wherein the substituent is selected from F, Cl, Br, $NO_2$, $R^8O-$, $R^8S(O)_m-$, $R^8C(O)NR^8-$, CN, $(R^8)_2N-C(NR^8)-$, $R^8C(O)-$, $R^8OC(O)-$, $N_3$, $—N(R^8)_2$, $R^9OC(O)NR^8-$ and $C_1-C_{20}$ alkyl, and
 d) $C_1-C_6$ alkyl substituted with an unsubstituted or substituted group selected from aryl and $C_3-C_{10}$ cycloalkyl;

$R^{5b}$ is selected from:
a) hydrogen, and
b) $C_1$–$C_3$ alkyl;

X-Y is

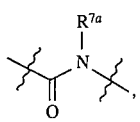 a)

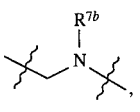 b)

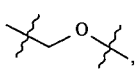 c)

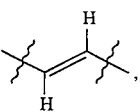 d)

or

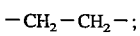 e)
$-CH_2-CH_2-$;

$R^{7a}$ is selected from
a) hydrogen,
b) unsubstituted or substituted aryl,
c) unsubstituted or substituted cycloalkyl, and
d) $C_1$–$C_6$ alkyl substituted with hydrogen or an unsubstituted or substituted group selected from aryl and cycloalkyl;

$R^{7b}$ is selected from
a) hydrogen,
b) unsubstituted or substituted aryl,
c) unsubstituted or substituted cycloalkyl,
d) $C_1$–$C_6$ alkyl substituted with hydrogen or an unsubstituted or substituted group selected from aryl and cycloalkyl,
e) a carbonyl group which is bonded to an unsubstituted or substituted group selected from aryl, cycloalkyl and $C_1$–Calkyl substituted with hydrogen or an unsubstituted or substituted group selected from aryl and cycloalkyl, and
f) a sulfonyl group which is bonded to an unsubstituted or substituted group selected from aryl, cycloalkyl and $C_1$–$C_6$ alkyl substituted with hydrogen or an unsubstituted or substituted group selected from aryl and cycloalkyl;

$R^8$ is independently selected from hydrogen, $C_1$–$C_6$ alkyl and aryl:

$R^9$ is independently selected from $C_1$–$C_6$ alkyl and aryl;

$Z^1$ and $Z^2$ are independently $H_2$ or O, provided that $Z^1$ is not O when

X-Y is $-C(O)N(R^{7a})$;

m is 0, 1 or 2; and t is 3;

or a pharmaceutically acceptable salt thereof.

3. A compound that inhibits farnesyl-protein transferase having the formula II:

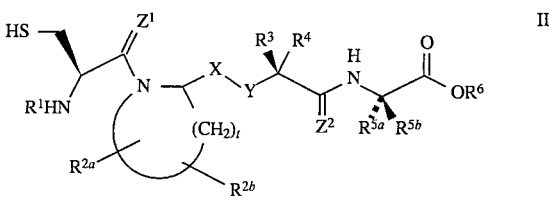 II wherein:
$R^1$ is selected from:
a) hydrogen,
b) $R^8S(O)_2$-, $R^8C(O)$-, $(R^8)_2NC(O)$- or $R^9OC(O)$-, and
c) $C_1$–$C_6$ alkyl unsubstituted or substituted by aryl, cycloalkyl, alkenyl, alkynyl, $R^8O$-, $R^8S(O)_m$-, $R^8C(O)NR^8$-, CN, $(R^8)_2N$-$C(NR^8)$-, $R^8C(O)$-, $R^8OC(O)$-, $N_3$, $-N(R^8)_2$, or $R^9OC(O)NR^8$-;

$R^{2a}$ is selected from:
a) hydrogen,
b) substituted or unsubstituted $C_1$–$C_{10}$ alkyl, $C_2$–$C_{10}$ alkenyl, $C_3$–$C_{10}$ cycloalkyl or aryl group, wherein the substituent is selected from F, Cl, Br, $NO_2$, $R^8O$-, $R^8S(O)_m$-, $R^8C(O)NR^8$-, CN, $(R^8)_2N$-$C(NR^8)$-, $R^8C(O)$-, $R^8OC(O)$-, $N_3$, $-N(R^8)_2$, $R^9OC(O)NR^8$- and $C_1$–$C_{20}$ alkyl,
c) $R^8O$-, $R^8S(O)_m$-, $R^8C(O)NR^8$-, CN, $NO_2$, $(R^8)_2N$-$C(NR^8)$-, $R^8C(O)$-, $R^8OC(O)$-, $N_3$, $-N(R^8)_2$, or $R^9OC(O)NR^8$-,
d) $C_1$–$C_6$ alkyl substituted with an unsubstituted or substituted group selected from aryl and $C_3$–$C_{10}$ cycloalkyl, and
e) a side chain of a naturally occurring amino acid, wherein the amino acid is selected from alanine, leucine, isoleucine, norleucine, valine and norvaline;

$R^{2b}$ is selected from:
a) hydrogen,
b) $C_1$–$C_6$ alkyl unsubstituted or substituted by alkenyl, $R^8O$-, $R^8S(O)_m$-, $R^8C(O)NR^8$-, CN, $(R^8)_2N$-$C(NR^8)$-, $R^8C(O)$-, $R^8OC(O)$-, $N_3$, $-N(R^8)_2$, or $R^9OC(O)NR^8$-,
c) aryl, cycloalkyl, alkenyl, $R^8O$-, $R^8S(O)_m$-, $R^8C(O)NR^8$-, CN, $NO_2$, $(R^8)_2N$-$C(NR^8)$-, $R^8C(O)$-, $R^8OC(O)$-, $N_3$, $-N(R^8)_2$, or $R^9OC(O)NR^8$-, and
d) $C_1$–$C_6$ alkyl substituted with an unsubstituted or substituted group selected from aryl and $C_3$–$C_{10}$ cycloalkyl;

$R^3$ and $R^4$ are independently selected from:
a) a side chain of a naturally occurring amino acid,
b) an oxidized form of a side chain of a naturally occurring amino acid which is:
i) methionine sulfoxide, or
ii) methionine sulfone,
c) substituted or unsubstituted $C_1$–$C_{20}$ alkyl, $C_2$–$C_{20}$ alkenyl, $C_3$–$C_{10}$ cycloalkyl or aryl group, wherein the substituent is selected from F, Cl, Br, $N(R^8)_2$, $NO_2$, $R^8O$-, $R^8S(O)_m$-, $R^8C(O)NR^8$-, CN, $(R^8)_2N$- $C(NR^8)$-, $R^8C(O)$-, $R^8OC(O)$-, $N_3$, $-N(R^8)_2$, $R^9OC(O)NR^8$- and $C_1$–$C_{20}$ alkyl, and
d) $C_1$–$C_6$ alkyl substituted with an unsubstituted or substituted group selected from aryl and $C_3$–$C_{10}$ cycloalkyl;or $R^3$ and $R^4$ are combined to form $-(CH_2)_s-$;

$R^{5a}$ and $R^{5b}$ are independently selected from:
a) a side chain of a naturally occurring amino acid, b) an oxidized form of a side chain of a naturally occurring amino acid which is:
  i) methionine sulfoxide, or
  ii) methionine sulfone,
c) substituted or unsubstituted $C_1$–$C_{20}$ alkyl, $C_2$–$C_{20}$ alkenyl, $C_3$–$C_{10}$ cycloalkyl or aryl group,
  wherein the substituent is selected from F, Cl, Br, $N(R^8)_2$, $NO_2$, $R^8O$-, $R^8S(O)_m$-, $R^8C(O)NR^8$-, CN, $(R^8)_2N$-$C(NR^8)$-, $R^8C(O)$-, $R^8OC(O)$-, $N_3$, —$N(R^8)_2$, $R^9OC(O)NR^8$- and $C_1$–$C_{20}$ alkyl, and
d) $C_1$–$C_6$ alkyl substituted with an unsubstituted or substituted group selected from aryl and $C_3$–$C_{10}$ cycloalkyl; or
  $R^{5a}$ and $R^{5b}$ are combined to form —$(CH_2)_s$—;
$R^6$ is
  a) substituted or unsubstituted $C_1$–$C_8$ alkyl, wherein the substituent on the alkyl is selected from:
    1) aryl,
    2) —$N(R^9)_2$,
    3) —$OR^8$, or
  b)

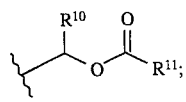

X-Y is

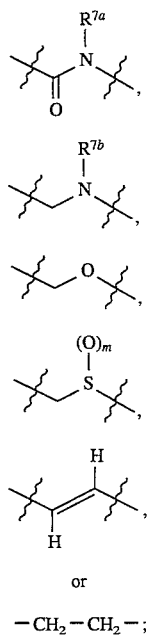

$R^{7a}$ is selected from
  a) hydrogen,
  b) unsubstituted or substituted aryl,
  c) unsubstituted or substituted cycloalkyl, and
  d) $C_1$–$C_6$ alkyl substituted with hydrogen or an unsubstituted or substituted group selected from aryl and cycloalkyl;
$R^{7b}$ is selected from
  a) hydrogen,
  b) unsubstituted or substituted aryl,
  c) unsubstituted or substituted cycloalkyl,
  d) $C_1$–$C_6$ alkyl substituted with hydrogen or an unsubstituted or substituted group selected from aryl and cycloalkyl, e) a carbonyl group which is bonded to an unsubstituted or substituted group selected from aryl, cycloalkyl and $C_1$–$C_6$ alkyl substituted with hydrogen or an unsubstituted or substituted group selected from aryl and cycloalkyl, and
f) a sulfonyl group which is bonded to an unsubstituted or substituted group selected from aryl, cycloalkyl and $C_1$–$C_6$ alkyl substituted with hydrogen or an unsubstituted or substituted group selected from aryl and cycloalkyl;
$R^8$ is independently selected from hydrogen, $C_1$–$C_6$ alkyl and aryl;
$R^9$ is independently selected from $C_1$–$C_6$ alkyl and aryl;
$R^{10}$ is independently selected from hydrogen and $C_1$–$C_6$ alkyl;
$R^{11}$ is independently selected from $C_1$–$C_6$ alkyl;
$Z^1$ and $Z^2$ are independently $H_2$ or O, provided that $Z_1$ is not O when X-Y is —$C(O)N(R^7a)$—;

m is 0, 1 or 2;
s is 4 or 5; and
t is 3;
or a pharmaceutically acceptable salt thereof.

4. A compound according to claim 3 which has the formula II:

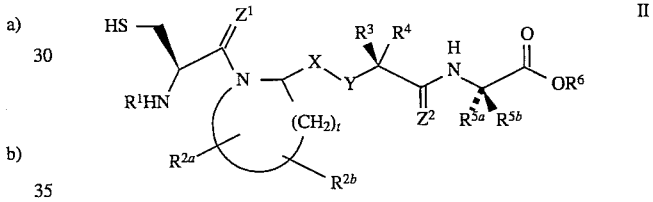

wherein:
$R^1$ is selected from:
  a) hydrogen,
  b) $R^8S(O)_2$-, $R^8C(O)$-, $(R^8)_2NC(O)$- or $R^9OC(O)$-, and
  c) $C_1$–$C_6$ alkyl unsubstituted or substituted by aryl, cycloalkyl, alkenyl, alkynyl, $R^8O$-, CN, $R^8S(O)_m$-, $R^8C(O)NR^8$-, $(R^8)_2N$-$C(NR^8)$-, $R^8C(O)$-, $R^8OC(O)$-, $N_3$, —$N(R^8)_2$, or $R^9OC(O)NR^8$-;
$R^{2a}$ is selected from:
  a) a side chain of a naturally occurring amino acid,
    wherein the amino acid is selected from alanine, leucine, isoleucine, norleucine, valine and norvaline;
  b) substituted or unsubstituted $C_1$–$C_{10}$ alkyl, $C_2$–$C_{10}$ alkenyl, $C_3$–$C_{10}$ cycloalkyl or aryl group.
    wherein the substituent is selected from F. Cl, Br, $NO_2$, $R^8O$-, $R^8S(O)_m$-, $R^8C(O)NR^8$-, CN, $(R^8)_2N$-$C(NR^8)$-, $R^8C(O)$-, $R^8OC(O)$-, $N_3$, —$N(R^8)_2$, $R^9OC(O)NR^8$- and $C_1$–$C_{20}$ alkyl, and
  c) $C_1$–$C_6$ alkyl substituted with an unsubstituted or substituted group selected from aryl and $C_3$–$C_{10}$ cycloalkyl;
$R^{2b}$ is selected from hydrogen and $C_1$–$C_6$ alkyl;
$R^3$ and $R^4$ are independently selected from:
  a) a side chain of a naturally occurring amino acid,
  b) an oxidized form of a side chain of a naturally occurring amino acid which is:
    i) methionine sulfoxide, or
    ii) methionine sulfone,
  c) substituted or unsubstituted $C_1$–$C_{10}$ alkyl, $C_2$–$C_{10}$ alkenyl, $C_3$–$C_{10}$ cycloalkyl or aryl group.

wherein the substituent is selected from F, Cl, Br, NO$_2$, R$^8$O-, R$^8$S(O)$_m$-, R$^8$C(O)NR$^8$-, CN, (R$^8$)$_2$N-C(NR$^8$)-, R$^8$C(O)-, R$^8$OC(O)-, N$_3$, —N(R$^8$)$_2$, R$^9$OC(O)NR$^8$- and C$_1$–C$_{20}$ alkyl, and d) C$_1$–C$_6$ alkyl substituted with an unsubstituted or substituted group selected from aryl and C$_3$–C$_{10}$ cycloalkyl;

R$_{5a}$ is selected from:
a) a side chain of a naturally occurring amino acid, wherein the amino acid is selected from methionine and glutamine,
b) an oxidized form of a side chain of a naturally occurring amino acid which is:
  i) methionine sulfoxide, or
  ii) methionine sulfone,
c) substituted or unsubstituted C$_1$–C$_{10}$ alkyl, C$_2$–C$_{10}$ alkenyl, C$_3$–C$_{10}$ cycloalkyl or aryl group,
wherein the substituent is selected from F, Cl, Br, NO$_2$, R$^8$O-, R$^8$S(O)$_m$-, R$^8$C(O)NR$^8$-, CN, (R$^8$)$_2$N-C(NR$^8$)-, R$^8$C(O)-, R$^8$OC(O)-, N$_3$, —N(R$^8$)$_2$, R$^9$OC(O)NR$^8$- and C$_1$–C$_{20}$ alkyl, and
d) C$_1$–C$_6$ alkyl substituted with an unsubstituted or substituted group selected from aryl and C$_3$–C$_{10}$ cycloalkyl;

R$^{5b}$ is selected from:
a) hydrogen, and
b) C$_1$–C$_3$ alkyl;

X-Y is

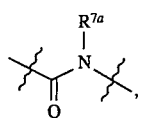 a)

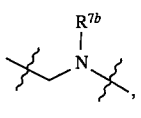 b)

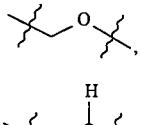 c)

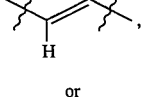 d)

or

—CH$_2$—CH$_2$—; e)

R$^6$ is
a) substituted or unsubstituted C$_1$–C$_8$ alkyl, wherein substituent on the alkyl is selected from:
  1) aryl,
  2) —N(R$^9$)$_2$,
  3) —OR$^8$, or
b)

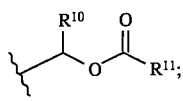

R$^{7a}$ is selected from
a) hydrogen,
b) unsubstituted or substituted aryl,
c) unsubstituted or substituted cycloalkyl, and d) C$_1$–C$_6$ alkyl substituted with hydrogen or an unsubstituted or substituted group selected from aryl and cycloalkyl;

R$^{7b}$ is selected from
a) hydrogen,
b) unsubstituted or substituted aryl,
c) unsubstituted or substituted cycloalkyl,
d) C$_1$–C$_6$ alkyl substituted with hydrogen or an unsubstituted or substituted group selected from aryl and cycloalkyl,
e) a carbonyl group which is bonded to an unsubstituted or substituted group selected from aryl, cycloalkyl and C$_1$–C$_6$ alkyl substituted with hydrogen or an unsubstituted or substituted group selected from aryl and cycloalkyl, and
f) a sulfonyl group which is bonded to an unsubstituted or substituted group selected from aryl, cycloalkyl and C$_1$–C$_6$ alkyl substituted with hydrogen or an unsubstituted or substituted group selected from aryl and cycloalkyl;

R$^8$ is independently selected from hydrogen, C$_1$–C$_6$ alkyl and aryl;
R$^9$ is independently selected from C$_1$–C$_6$ alkyl and aryl;
R$^{10}$ is independently selected from hydrogen and C$_1$–C$_6$ alkyl;
R$^{11}$ is 1,1-dimethylethyl;
Z$^1$ and Z$^2$ are independently H$_2$ or O, provided that Z$^1$ is not O when X-Y is —C(O)N(R$^7$a)-;

m is 0, 1 or 2; and
t is 3;
or a pharmaceutically acceptable salt thereof.

5. A compound which inhibits Ras farnesyl-transferase having the formula III:

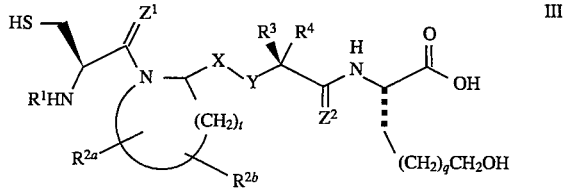 III wherein:
R$^1$ is selected from:
a) hydrogen,
b) R$^8$S(O)$_2$-, R$^8$C(O)-, (R$^8$)$_2$NC(O)- or R$^9$OC(O)-, and
c) C$_1$–C$_6$ alkyl unsubstituted or substituted by aryl, cycloalkyl, alkenyl, alkynyl, R$^8$O-, R$^8$S(O)$_m$-, R$^8$C(O)NR$^8$-, CN, (R$^8$)$_2$N-C(NR$^8$)-, R$^8$C(O)-, R$^8$OC(O)-, N$_3$, —N(R$^8$)$_2$, or R$^9$OC(O)NR$^8$-;

R$^{2a}$ is selected from:
a) hydrogen,
b) substituted or unsubstituted C$_1$–C$_{10}$ alkyl, C$_2$–C$_{10}$ alkenyl, C$_3$–C$_{10}$ cycloalkyl or aryl group, wherein the substituent is selected from F, Cl, Br, NO$_2$, R$^8$O-, R$^8$S(O)$_m$-, R$^8$C(O)NR$^8$-, CN, (R$^8$)$^2$N-C(NR$^8$)-, R$^8$C(O)-, R$^8$OC(O)-, N$_3$-, —N(R$^8$)$_2$, R$^9$OC(O)NR$^8$- and C$_1$–C$_{20}$ alkyl,
c) R$^8$O-, R$^8$S(O)$_m$, R$^8$C(O)NR$^8$-, CN, NO$_2$, (R$^8$)$_2$N-C(NR$^8$)-, R$^8$C(O)-, R$^8$OC(O)-, N$_3$, —N(R$^8$)$_2$, or R$^9$OC(O)NR$^8$-,
d) C$_1$–C$_6$ alkyl substituted with an unsubstituted or substituted group selected from aryl and C$_3$–C$_{10}$ cycloalkyl, and e) a side chain of a naturally occurring amino acid, wherein the amino acid is selected from alanine, leucine, isoleucine, norleucine, valine and norvaline;

$R^{2b}$ is selected from:
a) hydrogen,
b) $C_1-C_6$ alkyl unsubstituted or substituted by alkenyl, $R^8O-$, $R^8S(O)_m-$, $R^8C(O)NR^8-$, CN, $(R^8)_2N-C(NR^8)-$, $R^8C(O)-$, $R^8OC(O)-$, $N_3$, $-N(R^8)_2$, or $R^9OC(O)NR^8-$,
c) aryl, cycloalkyl, alkenyl, $R^8O-$, $R^8S(O)_m-$, $R^8C(O)NR^8-$, CN, $NO_2$, $(R^8)_2N-C(NR^8)-$, $R^8C(O)-$, $R^8OC(O)-$, $N_3$, $-N(R^8)_2$, or $R^9OC(O)NR^8-$, and
d) $C_1-C_6$ alkyl substituted with an unsubstituted or substituted group selected from aryl and $C_3-C_{10}$ cycloalkyl;

$R^3$ and $R^4$ are independently selected from:
a) a side chain of a naturally occurring amino acid,
b) an oxidized form of a side chain of a naturally occurring amino acid which is:
  i) methionine sulfoxide, or
  ii) methionine sulfone,
c) substituted or unsubstituted $C_1-C_{20}$ alkyl, $C_2-C_{20}$ alkenyl, $C_3-C_{10}$ cycloalkyl or aryl group, wherein the substituent is selected from F, Cl, Br, $N(R^8)^2$, $NO_2$, $R^8O-$, $R^8S(O)_m-$, $R^8C(O)NR^8-$, CN, $(R^8)_2N-C(NR^8)-$, $R^8C(O)-$, $R^8OC(O)-$, $N_3$, $-N(R^8)_2$, $R^9OC(O)NR^8-$ and $C_1-C_{20}$ alkyl, and
d) $C_1-C_6$ alkyl substituted with an unsubstituted or substituted group selected from aryl and $C_3-C_{10}$ cycloalkyl; or $R^3$ and $R^4$ are combined to form $-(CH_2)_s-$;

X-Y is

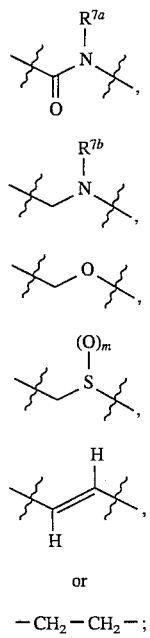

$R^{7a}$ is selected from
a) hydrogen,
b) unsubstituted or substituted aryl,
c) unsubstituted or substituted cycloalkyl, and
d) $C_1-C_6$ alkyl substituted with hydrogen or an unsubstituted or substituted group selected from aryl and cycloalkyl;

$R^{7b}$ is selected from
a) hydrogen,
b) unsubstituted or substituted aryl,
c) unsubstituted or substituted cycloalkyl,
d) $C_1-C_6$ alkyl substituted with hydrogen or an unsubstituted or substituted group selected from aryl and cycloalkyl,
e) a carbonyl group which is bonded to an unsubstituted or substituted group selected from aryl, cycloalkyl and $C_1-C_6$ alkyl substituted with hydrogen or an unsubstituted or substituted group selected from aryl and cycloalkyl, and
f) a sulfonyl group which is bonded to an unsubstituted or substituted group selected from aryl, cycloalkyl and $C_1-C_6$ alkyl substituted with hydrogen or an unsubstituted or substituted group selected from aryl and cycloalkyl;

$R^8$ is independently selected from hydrogen, $C_1-C_6$ alkyl and aryl;
$R^9$ is independently selected from $C_1-C_6$ alkyl and aryl;
$Z^1$ and $Z^2$ are independently $H_2$ or O, provided that $Z^1$ is not O when X-Y is $-C(O)N(R^{7a})-$;

m is 0, 1 or 2;
q is 0, 1 or 2;
s is 4 or 5; and
t is 3;

or a pharmaceutically acceptable salt thereof.

6. A compound according to claim 5 which has the formula III:

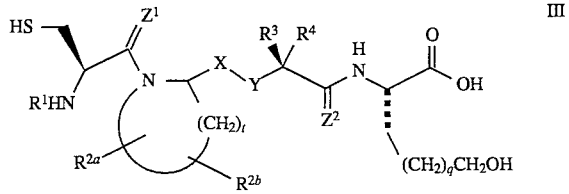

wherein:
$R^1$ is selected from:
a) hydrogen,
b) $R^8S(O)_2-$, $R^8C(O)-$, $(R^8)_2NC(O)-$ or $R^9OC(O)-$, and
c) $C_1-C_6$ alkyl unsubstituted or substituted by aryl, cycloalkyl, alkenyl, alkynyl, $R^8O-$, $R^8S(O)_m-$, $R^8C(O)NR^8-$, CN, $(R^8)_2N-C(NR^8)-$, $R^8C(O)-$, $R^8OC(O)-$, $N_3$, $-N(R^8)_2$, or $R^9OC(O)NR^8-$;

$R^{2a}$ is selected from:
a) a side chain of a naturally occurring amino acid, wherein the amino acid is selected from alanine, leucine, isoleucine, norleucine, valine and norvaline;
b) substituted or unsubstituted $C_1-C_{10}$ alkyl, $C_2-C_{10}$ alkenyl, $C_3-C_{10}$ cycloalkyl or aryl group, wherein the substituent is selected from F, Cl, Br, $NO_2$, $R^8O-$, $R^8S(O)_m-$, $R^8C(O)NR^8-$, CN, $(R^8)_2N-C(NR^8)-$, $R^8C(O)-$, $R^8OC(O)-$, $N_3$, $-N(R^8)_2$, $R^9OC(O)NR^8-$, $C_1-C_{20}$ alkyl, and
c) $C_1-C_6$ alkyl substituted with an unsubstituted or substituted group selected from aryl and $C_3-C_{10}$ cycloalkyl;

$R^{2b}$ is selected from hydrogen and $C_1-C_6$ alkyl;

$R^3$ and $R^4$ are independently selected from:
a) a side chain of a naturally occurring amino acid,
b) an oxidized form of a side chain of a naturally occurring amino acid which is:
  i) methionine sulfoxide, or ii) methionine sulfone, c) substituted or unsubstituted $C_1$–$C_{10}$ alkyl, $C_2$–$C_{10}$ alkenyl, $C_3$–$C_{10}$ cycloalkyl or aryl group,
wherein the substituent is selected from F, Cl, Br, $NO_2$, $R^8O$-, $R^8S(O)_m$-, $R^8C(O)NR^8$-, CN, $(R^8)_2N$-$C(NR^8)$-, $R^8C(O)$-, $R^8OC(O)$-, $N_3$, —$N(R^8)_2$, $R^9OC(O)NR^8$- and $C_1$–$C_{20}$ alkyl, and d) $C_1$–$C_6$ alkyl substituted with an unsubstituted or substituted group selected from aryl and $C_3$–$C_{10}$ cycloalkyl;

X-Y is

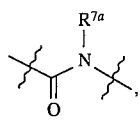   a)

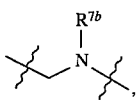   b)

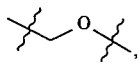   c)

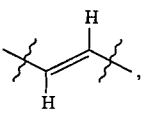   d)

or

—$CH_2$—$CH_2$—;   e)

$R^{7a}$ is selected from a) hydrogen, b) unsubstituted or substituted aryl, c) unsubstituted or substituted cycloalkyl, and d) $C_1$–$C_6$ alkyl substituted with hydrogen or an unsubstituted or substituted group selected from aryl and cycloalkyl;

$R^{7b}$ is selected from a) hydrogen, b) unsubstituted or substituted aryl, c) unsubstituted or substituted cycloalkyl, d) $C_1$–$C_6$ alkyl substituted with hydrogen or an unsubstituted or substituted group selected from aryl and cycloalkyl, e) a carbonyl group which is bonded to an unsubstituted or substituted group selected from aryl, cycloalkyl and $C_1$–$C_6$ alkyl substituted with hydrogen or an unsubstituted or substituted group selected from aryl and cycloalkyl, and f) a sulfonyl group which is bonded to an unsubstituted or substituted group selected from aryl, cycloalkyl and $C_1$–$C_6$ alkyl substituted with hydrogen or an unsubstituted or substituted group selected from aryl and cycloalkyl;

$R^8$ is independently selected from hydrogen, $C_1$–$C_6$ alkyl and aryl;

$R^9$ is independently selected from $C_1$–$C_6$ alkyl and aryl;

$Z^1$ and $Z^2$ are independently $H_2$ or O, provided that $Z^1$ is not O when

X-Y is —$C(O)N(R^{7a})$-;

m is 0, 1 or 2;

q is 0, 1 or 2; and t is 3:

or a pharmaceutically acceptable salt thereof.

7. A compound which inhibits farnesyl-protein transferase which is:

N-[1-(2(R)-amino-3-mercaptopropyl)-2(S)-pyrrolidinylmethyl]-N-(1-naphthylmethyl)glycyl-methionine

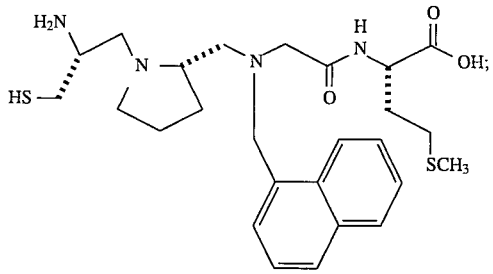

N-[1-(2(R)-amino-3-mercaptopropyl)-2(S)-pyrrolidinylmethyl]-N-(1-naphthylmethyl)glycyl-methionine methyl ester

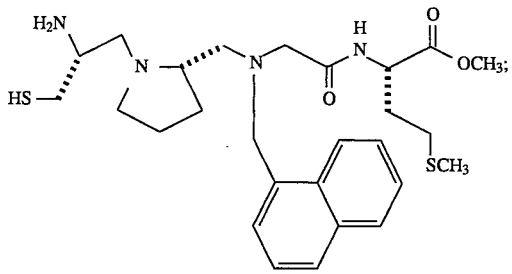

2(S)-[[1-[2(R)-Amino-3-mercapto]propyl]-2(S)-(pyrrolidinyl)methyloxy]-3-phenylpropionyl-methionine; or

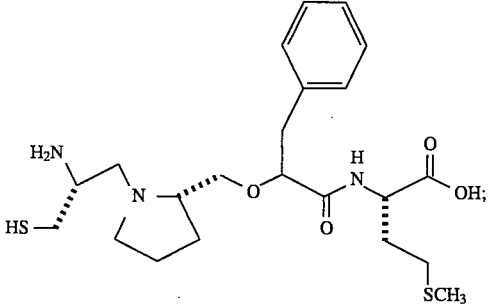

2(S)-[[1-[2(S)-Amino-3-mercapto]propyl]-2(S)-(pyrrolidinyl)methyloxy]-3-phenylpropionyl-methionine;

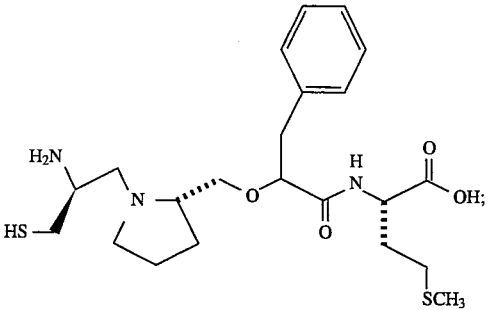

or a pharmaceutically acceptable salt thereof.

8. A pharmaceutical composition comprising a pharmaceutical carrier, and dispersed therein, a therapeutically effective amount of a compound of claim 1.

9. A pharmaceutical composition comprising a pharmaceutical carrier, and dispersed therein, a therapeutically effective amount of a compound of claim 3.

10. A pharmaceutical composition comprising a pharmaceutical carrier, and dispersed therein, a therapeutically effective amount of a compound of claim 5.

11. A pharmaceutical composition comprising a pharmaceutical carrier, and dispersed therein, a therapeutically effective amount of a compound of claim 7.

12. A method for inhibiting farnesylation of Ras protein which comprises administering to a mammal in need thereof a therapeutically effective amount of the composition of claim 8.

13. A method for inhibiting farnesylation of Ras protein which comprises administering to a mammal in need thereof a therapeutically effective amount of the composition of claim 9.

14. A method for inhibiting farnesylation of Ras protein which comprises administering to a mammal in need thereof a therapeutically effective amount of the composition of claim 10.

15. A method for inhibiting farnesylation of Ras protein which comprises administering to a mammal in need thereof a therapeutically effective amount of the composition of claim 11.

16. A method for treating cancer which comprises administering to a mammal in need thereof a therapeutically effective amount of a composition of claim 8.

17. A method for treating cancer which comprises administering to a mammal in need thereof a therapeutically effective amount of a composition of claim 9.

18. A method for treating cancer which comprises administering to a mammal in need thereof a therapeutically effective amount of a composition of claim 10.

19. A method for treating cancer which comprises administering to a mammal in need thereof a therapeutically effective amount of a composition of claim 11.

* * * * *

UNITED STATES PATENT AND TRADEMARK OFFICE
CERTIFICATE OF CORRECTION

PATENT NO. : 5,571,835
DATED : November 5, 1996
INVENTOR(S) : Neville J. Anthony, S. Jane deSolms and Samuel L. Graham It is certified that error appears in the above-indentified patent and that said Letters Patent is hereby corrected as shown below:

In Column 47, between lines 46 and 54, the structure should read:

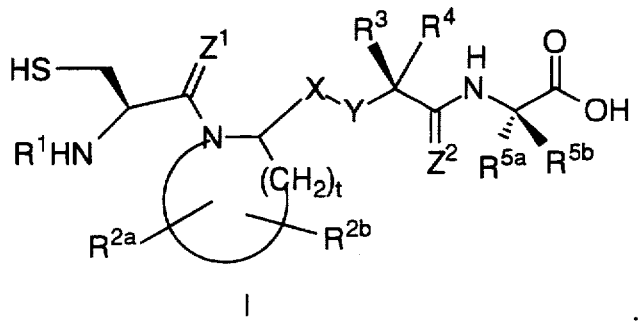

In Column 47, line 60 should read:

-- cycloalkyl, alkenyl, alkynyl, $R^8O-$, $R^8S(O)_m-$, --.

In Column 48, line 1, the substituent after "Cl" should read: -- Br, --.

In Column 48, line 36, the substituent after "$R^8O-$," should read:

-- $R^8S(O)_m-$, --.

In Column 49, line 60 should read: -- X-Y is $-C(O)N(R^{7a})-$; --.

UNITED STATES PATENT AND TRADEMARK OFFICE
CERTIFICATE OF CORRECTION

PATENT NO. : 5,571,835
DATED : November 5, 1996
INVENTOR(S) : Neville J. Anthony, S. Jane deSolms and Samuel L. Graham It is certified that error appears in the above-indentified patent and that said Letters Patent is hereby corrected as shown below:

In Column 50, line 25 should read:

-- alkenyl, $C_3$-$C_{10}$ cycloalkyl or aryl group, --.

In Column 51, line 46 should begin:

-- $C_1$-$C_6$ alkyl --.

In Column 51, line 63 should read:

-- X-Y is -C(O)N($R^{7a}$)-; --.

In Column 54, line 17, between "that" and "is", should be -- $Z^1$ --.

In Column 54, line 20 should read: -- X-Y is -C(O)N$R^{7a}$)-; --.

In Column 55, line 8 should read: -- $R^{5a}$ is selected from: --.

UNITED STATES PATENT AND TRADEMARK OFFICE
CERTIFICATE OF CORRECTION

PATENT NO. : 5,571,835
DATED : November 5, 1996
INVENTOR(S) : Neville J. Anthony, S. Jane deSolms and Samuel L. Graham It is certified that error appears in the above-indentified patent and that said Letters Patent is hereby corrected as shown below:

In Column 56, line 29 should read: -- X-Y is -C(O)N($R^{7a}$)-; --.

In Column 56, line 58, after "CN," should read: -- ($R^8$)$_2$N-C(N$R^8$)-, --.

In Column 56, line 61, after "c) $R^8$O-," should read: -- $R^8$S(O)$_m$-, --.

In Column 57, line 25, the first substituent should read: -- N($R^8$)$_2$, --.

In Column 58, line 21 should read: -- X-Y is -C(O)N($R^{7a}$)-; --.

Signed and Sealed this

Eighteenth Day of March, 1997

Attest:

BRUCE LEHMAN

Attesting Officer

Commissioner of Patents and Trademarks